United States Patent
Kyriazopoulou-Panagiotopoulou et al.

(10) Patent No.: US 12,046,330 B2
(45) Date of Patent: *Jul. 23, 2024

(54) SYSTEMS AND METHODS FOR IDENTIFYING STRUCTURAL VARIANTS

(71) Applicant: 10X Genomics, Inc., Pleasanton, CA (US)

(72) Inventors: Sofia Kyriazopoulou-Panagiotopoulou, Redwood City, CA (US); Patrick Marks, San Francisco, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 870 days.

This patent is subject to a terminal disclaimer.

(21) Appl. No.: 16/934,994

(22) Filed: Jul. 21, 2020

(65) Prior Publication Data

US 2021/0134393 A1    May 6, 2021

Related U.S. Application Data

(63) Continuation of application No. 15/692,316, filed on Aug. 31, 2017, now Pat. No. 10,748,643.

(51) Int. Cl.
*G01N 33/48* (2006.01)
*C40B 40/06* (2006.01)
(Continued)

(52) U.S. Cl.
CPC .............. *G16B 40/00* (2019.02); *C40B 40/06* (2013.01); *G06F 18/24* (2023.01); *G06N 7/01* (2023.01);
(Continued)

(58) Field of Classification Search
CPC .......... G16B 40/00; G16B 5/00; G16B 20/00; G16B 30/20; G16B 25/00; G06F 18/24; G06N 7/01; C12Q 1/6809; C12Q 1/6869
See application file for complete search history.

(56) References Cited

U.S. PATENT DOCUMENTS

| | | |
|---|---|---|
| 9,644,204 B2 | 5/2017 | Hindson et al. |
| 10,366,777 B2 | 7/2019 | Kyriazopoulou-Panagiotopo et al. |

(Continued)

OTHER PUBLICATIONS

Abecasis et al., 2012, "An integrated map of genetic variation from 1,092 human genomes," Nature. 491 (7422): 56-65.
(Continued)

*Primary Examiner* — Russell S Negin

(57) ABSTRACT

Systems and methods for analyzing first and second strings against a ground truth string are provided. A construct representing a plurality of components is obtained, each component for a different portion of the truth string. The construct comprises a plurality of measurement string sampling pools each having an identifier and a corresponding plurality of measurement samplings corresponding to one or two of the components. Each sampling has the identifier and a portion of the first or second string. Samplings are assigned to first, second or third classes when coding a portion of the first string, second string, or both the first and second string. First and second positions are tested for sequence events by calculating a plurality of sequence event models using assumptions on the components having samplings encompassing the first and second positions and class assignments. These assumptions are updated using the calculated models and the models are recalculated.

22 Claims, 12 Drawing Sheets

(51) Int. Cl.
| | |
|---|---|
| *G01N 33/50* | (2006.01) |
| *G06F 18/24* | (2023.01) |
| *G06N 7/01* | (2023.01) |
| *G16B 5/00* | (2019.01) |
| *G16B 20/00* | (2019.01) |
| *G16B 30/20* | (2019.01) |
| *G16B 40/00* | (2019.01) |
| *C12Q 1/6809* | (2018.01) |
| *C12Q 1/6869* | (2018.01) |
| *G06N 5/01* | (2023.01) |
| *G06N 5/025* | (2023.01) |
| *G16B 25/00* | (2019.01) |

(52) U.S. Cl.
CPC ............... *G16B 5/00* (2019.02); *G16B 20/00* (2019.02); *G16B 30/20* (2019.02); *B01J 2219/00317* (2013.01); *C12Q 1/6809* (2013.01); *C12Q 1/6869* (2013.01); *G06N 5/01* (2023.01); *G06N 5/025* (2013.01); *G16B 25/00* (2019.02)

(56) References Cited

U.S. PATENT DOCUMENTS

| | | | |
|---|---|---|---|
| 10,748,643 | B2 * | 8/2020 | Kyriazopoulou-Panagiotopoulou ... G16B 20/00 |
| 2003/0177095 | A1 | 9/2003 | Zorab et al. |
| 2010/0105112 | A1 | 4/2010 | Holtze et al. |
| 2014/0155295 | A1 | 6/2014 | Hindson et al. |
| 2014/0378345 | A1 | 12/2014 | Hindson et al. |
| 2015/0376605 | A1 | 12/2015 | Jarosz et al. |

OTHER PUBLICATIONS

Bentley et al., 2008, Accurate whole human genome sequencing using reversible terminator chemistry, Nature 456:53-59.

Chen et al., 2009, "BreakDancer: an algorithm for high-resolution mapping of genomic structural variation," Nature Methods 6(9), pp. 677-681.

Craig et al., "Ordering of cosmid clones covering the Herpes simplex virus type I (HSV-I) genome: a test case for fingerprinting by hybridization," Nucleic Acid Research, 1990, vol. 18, No. 9, 2653-2660.

Eid et al., "Real-time sequencing form single polymerase molecules," Science 323:133-138.

Holmes, Ian, "Using Evolutionary Expectation Maximization to Estimate Indel Rates", Bioinformatics, vol. 21, No. 10 2005, p. 2294-2300 (2005).

Layer et al., 2014, "Lumpy: A probabilistic framework for structural variant discovery," Genome Biology 15(6):R84.

Lippert et al., 2002, "Algorithmic strategies for the single nucleotide polymorphism haplotype assembly problem," Brief. Bionform 3:23-31.

Margulies et al., 2005, "Genome sequencing in microfabricated high-density picoliter reactors," Nature 437:376-380.

Miller et al., 2010, "Assembly algorithms for next generation sequencing data," Genomics 95, pp. 315-327.

Pushkarev et al., 2009, "Single-molecule sequencing of an individual human genome," Nature Biotech 17:847-850.

Shendure et al., 2005, "Accurate Multiplex Polony Sequencing of an Evolved bacterial Genome" Science 309:1728-1732.

U.S. Appl. No. 61/940,318, filed Feb. 14, 2014.
U.S. Appl. No. 61/991,018, filed May 9, 2014.
U.S. Appl. No. 62/017,589, filed Jun. 26, 2014.
U.S. Appl. No. 62/072,214, filed Oct. 29, 2014.
U.S. Appl. No. 62/113,693, filed Feb. 9, 2015.

* cited by examiner

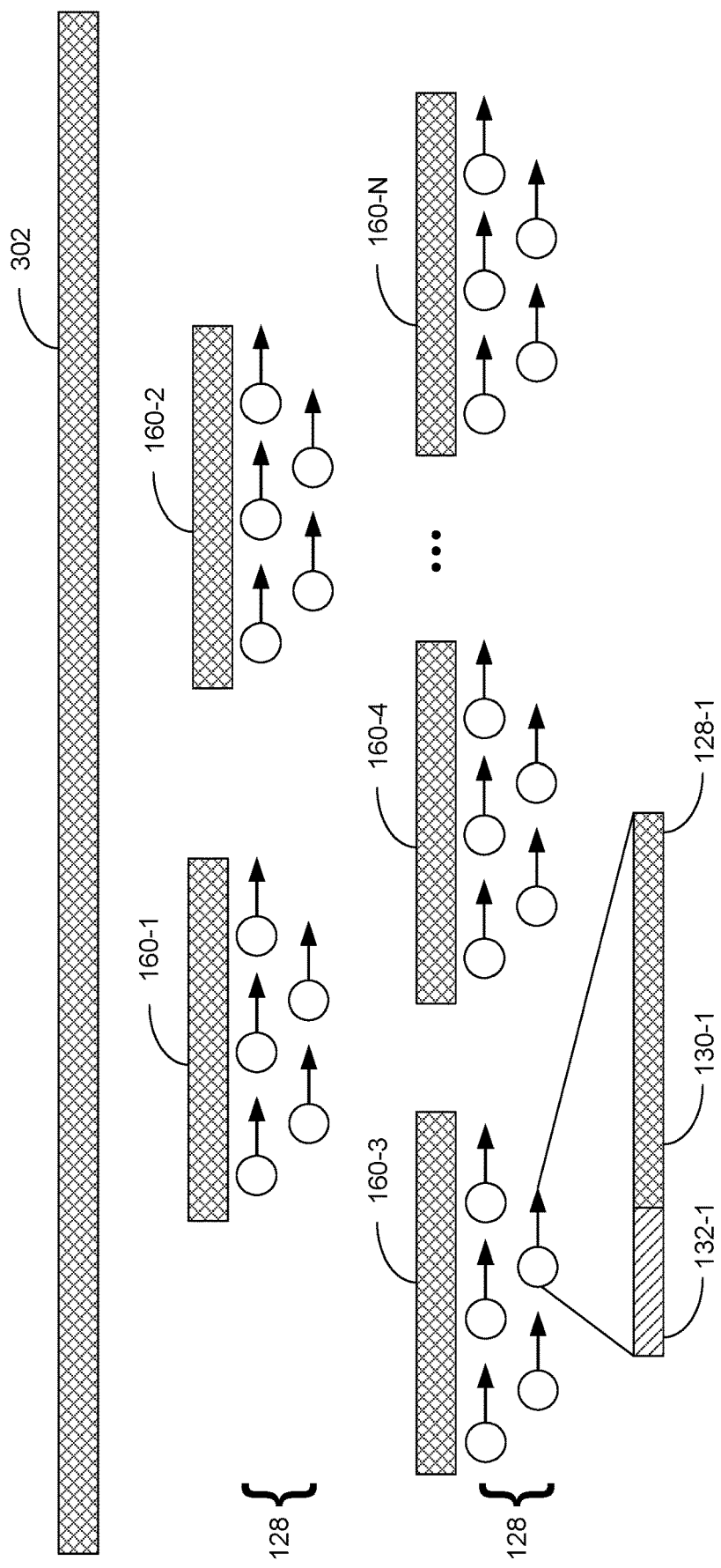

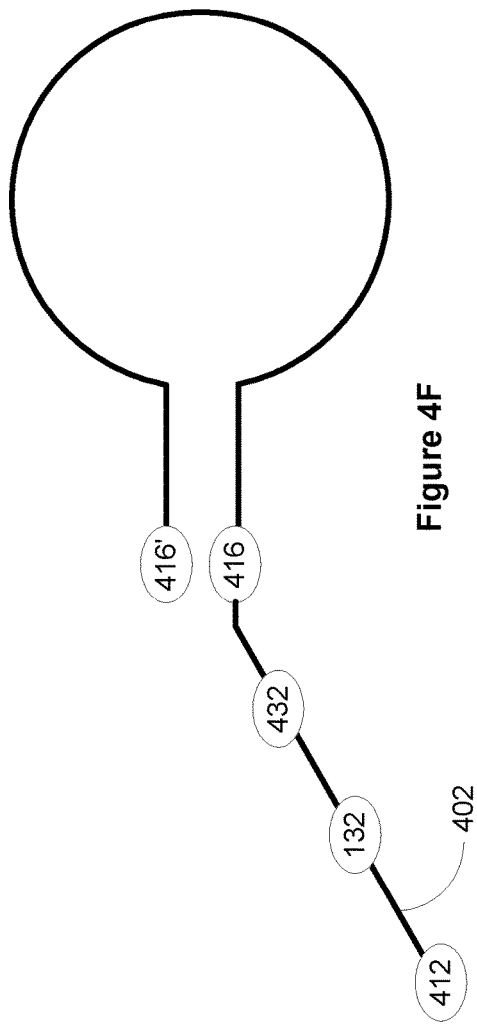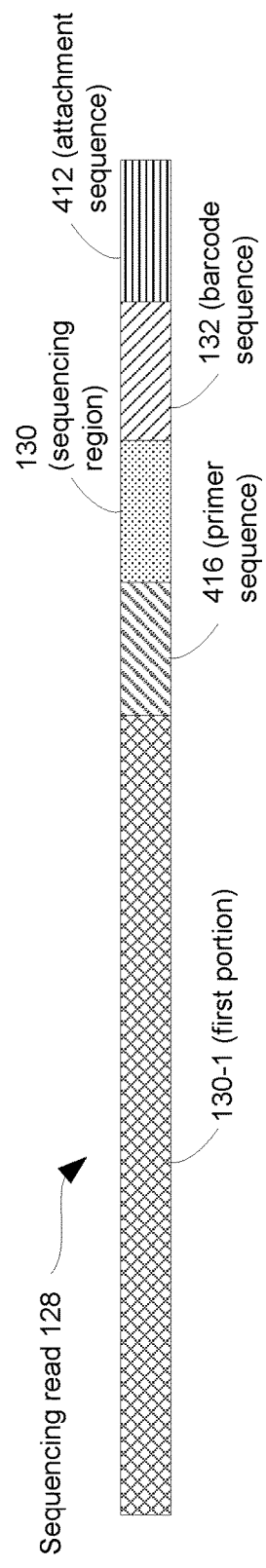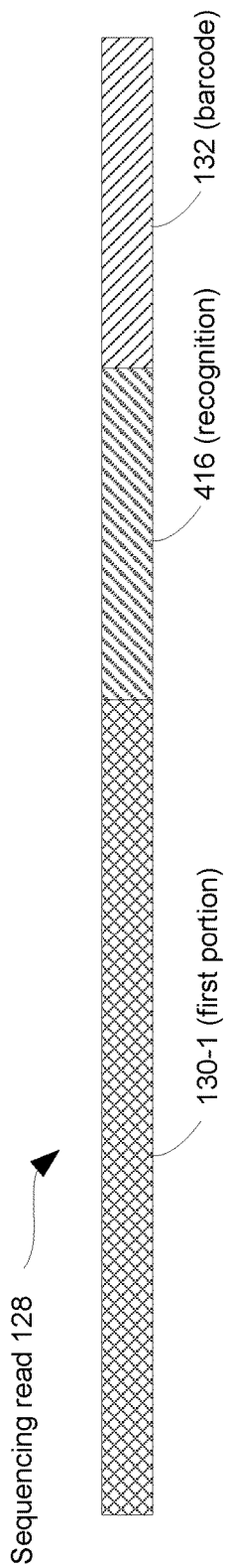

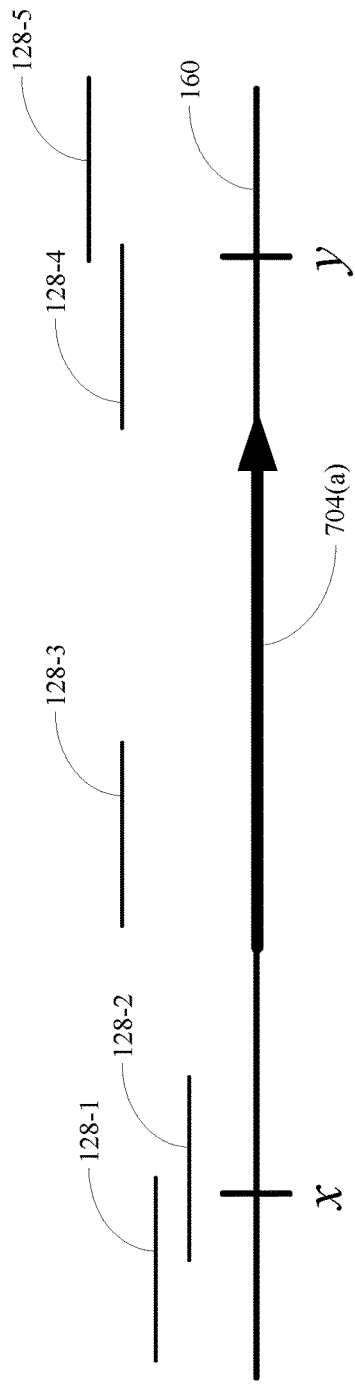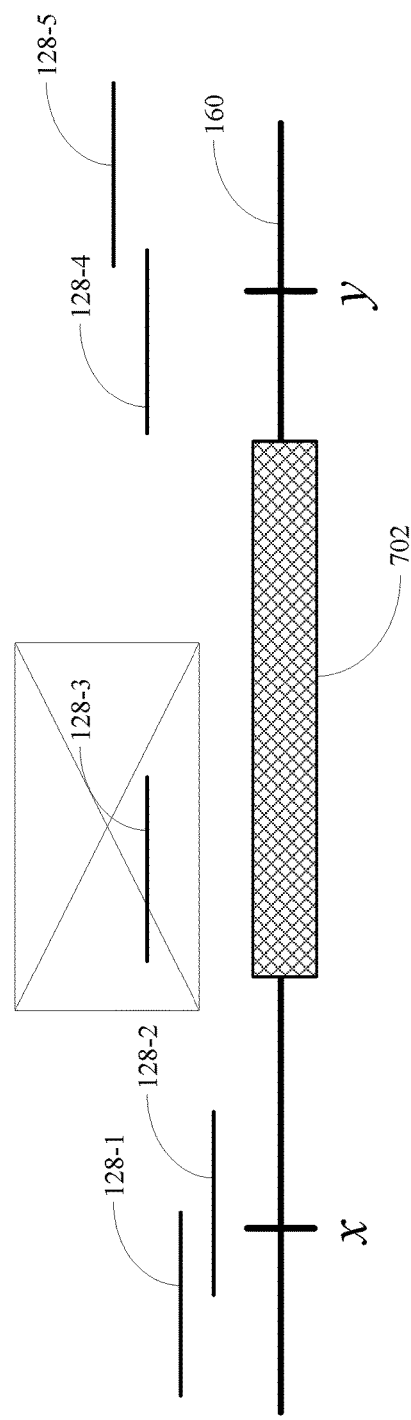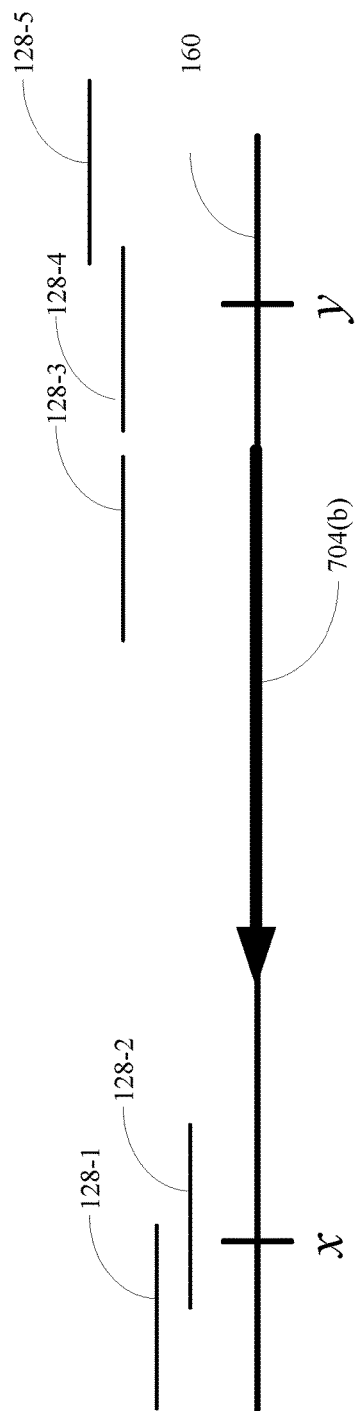

SYSTEMS AND METHODS FOR IDENTIFYING STRUCTURAL VARIANTS

CROSS-REFERENCE TO RELATED APPLICATION

This application is continuation of U.S. application Ser. No. 15/692,316, filed Aug. 31, 2017, which is herein incorporated by reference.

TECHNICAL FIELD

This specification describes technologies relating to determining the integrity of a first query string and a second query string with respect to a ground truth string through an expectation-maximization method.

BACKGROUND

Haplotype assembly from experimental data obtained from human genomes sequenced using massively parallelized sequencing methodologies has emerged as a prominent source of genetic data. Such data serves as a cost-effective way of implementing genetics based diagnostics as well as human disease study, detection, and personalized treatment.

The long-range information provided by platforms such as those disclosed in U.S. Patent Application No. 62/072,214, filed Oct. 29, 2014, entitled "Analysis of Nucleic Acid Sequences" greatly facilitates the detection of large-scale structural variations of the genome, such as translocations, large deletions, or gene fusions. Other examples include, but are not limited to the sequencing-by-synthesis platform (ILLUMINA), Bentley et al., 2008, "Accurate whole human genome sequencing using reversible terminator chemistry, Nature 456:53-59; sequencing-by-litigation platforms (POLONATOR; ABI SOLiD), Shendure et al., 2005, "Accurate Multiplex Polony Sequencing of an Evolved bacterial Genome" Science 309:1728-1732; pyrosequencing platforms (ROCHE 454), Margulies et al., 2005, "Genome sequencing in microfabricated high-density picoliter reactors," Nature 437:376-380; and single-molecule sequencing platforms (HELICOS HELISCAPE); Pushkarev et al., 2009, "Single-molecule sequencing of an individual human genome," Nature Biotech 17:847-850, (PACIFIC BIOSCIENCES) Eid et al., "Real-time sequencing form single polymerase molecules," Science 323:133-138, each of which is hereby incorporated by reference in its entirety.

Several algorithms have been developed for detecting such events from whole genome sequencing (WGS) data. See, for example, Chen et al., 2009, "BreakDancer: an algorithm for high-resolution mapping of genomic structural variation," Nature Methods 6(9), pp, 677-681 and Layer et al., 2014, "LUMPY: A probabilistic framework for structural variant discovery," Genome Biology 15(6):R84. The goal of these algorithms is to detect the endpoints of structural variants (e.g., the endpoints of a deletion or a gene fusion). These endpoints are also referred to as "breakpoints" and the terms endpoints and breakpoints are used interchangeably. In order to detect breakpoints, existing algorithms rely on the detection of read pairs that are mapped to the genome at unexpected orientations with respect to each other or at unexpected distances (too far from each other or too close to each other relative to the insert size). This implies that, in order for the breakpoint to be detected by conventional algorithms, it must be spanned by read pairs. This limitation makes existing algorithms not applicable to targeted sequencing data, such as whole exome sequencing (WES) data. This is because the breakpoints would be spanned by read pairs only if they were very close to the target regions. This is usually not the case. For example many gene fusions in cancer happen on gene introns rather than exons, so they would not be detectable with WES.

The availability of haplotype data spanning large portions of the human genome, the need has arisen for ways in which to efficiently work with this data in order to advance the above stated objectives of diagnosis, discovery, and treatment, particularly as the cost of whole genome sequencing for a personal genome drops below $1000. To computationally assemble haplotypes from such data, it is necessary to disentangle the reads from the two haplotypes present in the sample and infer a consensus sequence for both haplotypes. Such a problem has been shown to be NP-hard. See Lippert et al., 2002, "Algorithmic strategies for the single nucleotide polymorphism haplotype assembly problem," Brief. Bionform 3:23-31, which is hereby incorporated by reference.

Given the above background, what is needed in the art are improved systems and methods for determining the integrity of a first query string and a second query string with respect to a ground truth string (e.g., haplotype phasing and structural variant detection using sequencing data) from parallelized sequencing methodologies.

SUMMARY

Technical solutions (e.g., computing systems, methods, and non-transitory computer readable storage mediums) for determining the integrity of a first query string and a second query string with respect to a ground truth string through an expectation-maximization method. With platforms such as those disclosed in U.S. Provisional Patent Application No. 62/072,214, filed Oct. 29, 2014, entitled "Analysis of Nucleic Acid Sequences," or U.S. Provisional Patent Application 62/113,693, entitled "Systems and Methods for Determining Structural Variation," filed Feb. 9, 2015, each of which is hereby incorporated by reference, the genome is fragmented and partitioned and barcoded prior to the target identification. Therefore the integrity of the barcode information is maintained across the genome. The barcode information is used to determine the integrity of a first query string and a second query string with respect to a ground truth string through an expectation-maximization method. For instance, the barcode information is used to identify potential structural variation breakpoints by detecting regions of the genome that show significant barcode overlap.

The following presents a summary of the invention in order to provide a basic understanding of some of the aspects of the invention. This summary is not an extensive overview of the invention. It is not intended to identify key/critical elements of the invention or to delineate the scope of the invention. Its sole purpose is to present some of the concepts of the invention in a simplified form as a prelude to the more detailed description that is presented later.

Various embodiments of systems, methods and devices within the scope of the appended claims each have several aspects, no single one of which is solely responsible for the desirable attributes described herein. Without limiting the scope of the appended claims, some prominent features are described herein. After considering this discussion, and particularly after reading the section entitled "Detailed Description" one will understand how the features of various embodiments are used.

One aspect of the present disclosure provides a computing system that comprises one or more processors and memory.

The memory stores one or more programs to be executed by the one or more processors. The one or more programs comprise instructions for determining the integrity of first and second strings with respect to a ground truth string through a two phase method. Here, the ground truth string corresponds to an entirety of the first string and an entirety of the second string. The first string is not fully determined and the second string is also not fully determined, meaning that at least portions of the first string and the second string are not measured or known. The two phase method comprises obtaining a construct that represents a plurality of components. Each respective component in the plurality of components maps to a different contiguous portion of the ground truth string and represents less than one percent of the ground truth string. The construct comprises a plurality of measurement string sampling pools. Each measurement string sampling pool is (i) characterized by a different identifier in a plurality of identifiers and (ii) comprises a corresponding plurality of measurement string samplings. Each respective measurement string sampling in the corresponding plurality of measurement string samplings of a measurement string sampling pool in the plurality of measurement string sampling pools (i) is obtained from an optical measurement device and (ii) includes the same identifier string in addition to a coding string that consists of a portion of the first string or the second string.

Each respective measurement string sampling in the plurality of measurement string samplings of a measurement string sampling pool in the plurality of measurement string sampling pools is assigned to (i) a first class when the coding region of the respective measurement string sampling matches a portion of the first string, (ii) a second class when the coding region of the respective sampling matches a portion of the second string or (iii) a third class when the coding region of the respective measurement string sampling matches the portion of the first string as well as the portion of the second string. The plurality of measurement string samplings across each respective measurement string sampling pool in the plurality of measurement string sampling pools collectively forms a Poisson or near Poisson distribution of measurement string samplings across both the first string and the second string. In some embodiments, at least some of the measurement string samplings in the plurality of measurement string sampling pools have not been assigned to the first class, the second class, or the third class with absolute certainty.

Each plurality of measurement string samplings represents a single corresponding component in the plurality of components or two discrete corresponding components in the plurality of components. In some embodiments, the data construct does not include measurement string samplings for at least a predetermined portion of each component in the plurality of components.

The method continues with the identification of a first position in the ground truth string and a second position in the ground truth string. Because the ground truth string corresponds to the first and second string, the first and second string also includes the first and second positions.

The method continues by calculating, as part of a first phase of the two phase method, an initial basis of a sequence event arising between the first position and the second position in the first string or the second string using each of a plurality of models and an initial assumption of (i) the number of components that contribute to each pool of measurement string samplings that includes measurement string samplings that collectively encompass the first position or the second position and (ii) the class assignment of the measurement string samplings that map onto components that overlap the first position or the second position. Each model in the plurality of models posits an observed distribution of measurement string samplings in the construct across the portion of the ground truth string that is bounded by the first position and the second position against an expected distribution of measurement string samplings in the construct across the ground truth string upon introduction of a sequence event.

A first model in the plurality of models assumes that no sequence event occurs between the first position and the second position in the first string or the second string. A second model in the plurality of models assumes that a sequence event occurs between the first position and the second position in both the first string and the second string. A third model in the plurality of models assumes that a sequence event occurs between the first position and the second position in only one of the first string and the second string but not the other of the first string and the second string.

The method continues by adjusting, as part of the second phase of the two phase method, the initial assumption of (i) the number of components that contribute to each pool of measurement string samplings that includes measurement string samplings that map to components that overlap the first position or the second position and (ii) the class assignment of the measurement string samplings that map onto components that overlap the first position or the second position using the calculated basis of the sequence event arising between the first position and the second position in the first string or the second string from each of the plurality of models.

The method continues by repeating the calculation of the models and the adjusting the initial assumptions until a convergence criterion is satisfied thereby determining the integrity of a first string and the second string with respect to the ground truth string.

In some embodiments, the identifying the first position in the ground truth string and the second position in the ground truth string is performed on the basis that there is at least a threshold probability that a sequence event occurs in the first string or the second string between the first position and the second position. In such embodiments a check for this threshold probability is performed by the method based upon an extent of overlap between measurement string samplings with common identifiers that map to the first position and the second position in the construct.

In some embodiments the first string, the second string, the reference sequence, each component in the plurality of components, and each measurement string sampling in each plurality of measurement string samples is a base-four string. For example, in some embodiments, each position in the first string, the second string, the reference sequence, each component in the plurality of components, and each measurement string sampling in each plurality of measurement string samples is one of the four possible nucleotides adenosine ("A"), thymine ("T"), cytosine ("C"), and guanine ("G").

In some embodiments, the ground truth string, the first string and the second string each include more than $3 \times 10^9$ positions. In some embodiments, each respective component in the plurality of components comprises between 25,000 and 100,000 positions. In some embodiments, there are more than twenty components in the plurality of components that map onto each position of the ground truth string.

In some embodiments, less than fifty percent of a component in the plurality of components is represented by measurement string samples in the plurality of measurement string sampling pools.

In some embodiments, less than fifty percent of each component in the plurality of components is represented by measurement string samples in the plurality of measurement string sampling pools.

In some embodiments, less than thirty percent of each component in the plurality of components is represented by measurement string samples in the plurality of measurement string sampling pools.

In some embodiments, each respective model m in the plurality of models is computed as $\Sigma_b \log P(D_b; m)$, where $\Sigma_b \log P(D_b; m)$ is a summation of a plurality of probabilities for a plurality of measurement string sampling pools that span the first and second position, each respective measurement string sampling pool in the plurality of measurement string sampling pools characterized by a different unique identifier b, and each probability in the plurality of probabilities is the probability of the observed spacing of measurement string samplings in the measurement string sampling pool having the common identifier b given model m.

In some embodiments, the first model comprises computing:

$$\prod_b \sum_{c=1}^{2} P(D_b \mid M_b = c, R_b) P(M_b = c)$$

wherein each b is a different identifier for a measurement string sampling pool that comprises measurement string samplings that encompass the first position and the second position, $P(M_b=1)$ is the probability that the measurement string sampling pool that comprises measurement string samplings for identifier b arises from a single component, $P(M_b=2)$ is the probability that the measurement string sampling pool that comprises measurement string samplings for identifier b arises from two different components, $P(D_b|M=1; R_b)=P_m(n, d)$ for a respective measurement string sampling pool having the common identifier b wherein, n is the number of measurement string samplings in the measurement string sampling pool for identifier b, $M_b=1$ indicates that the measurement string sampling pool for identifier b is deemed to map to a single component in the plurality of component, d is a length of the component, and $P(D_b|M_b=2; R_b)=$ $$\sum_{k=2}^{n-1} P(D_{b_1 \ldots k} \mid M_{b_1 \ldots k} = 1; R_{b_1 \ldots k})$$

$$P(D_{b_{k+1} \ldots n} \mid M_{b_{k+1} \ldots n} = 1; R_{b_{k+1} \ldots n})$$

wherein the measurement string samplings $b_1 \ldots k$ are deemed to map onto a first component and the measurement string samplings $b_{k+1} \ldots n$ are deemed to map onto a second component.

In some embodiments, the second model comprises computing:

$$\prod_b \sum_{c=1}^{2} P(D_b \mid M_b = c, SV_b^{x,y}) P(M_b = c)$$

where each b is a different identifier for a measurement string sampling pool that comprises measurement string samplings that encompass the first position and the second position, $P(D_b|M_b=1; SV_b^{x,y})$ is the probability that a sequence event occurs between the first position and the second position in both the first string and the second string assuming that the measurement string sampling pool that comprises measurement string samplings for identifier b arises from a single component, $P(M_b=1)$ is the probability that the measurement string sampling pool that comprises measurement string samplings for identifier b arises from a single component, and $P(M_b=2)$ is the probability that the measurement string sampling pool that comprises measurement string samplings for identifier b arises from two different components.

In some embodiments, the second model is computed separately for at least two different possible sequence events in the group consisting of a deletion between the first and second position, an inversion of a region between the first and second position, a duplication between the first and second position, and a translocation between the first and second position.

In some embodiments, the second model is computed separately for at least three different possible sequence events in the group consisting of a deletion between the first and second position, an inversion of a region between the first and second position, a duplication between the first and second position, and a translocation between the first and second position.

In some embodiments, the second model is computed separately for (i) a deletion between the first and second position, (ii) an inversion of a region between the first and second position, (iii) a duplication between the first and second position, and (iv) a translocation between the first and second position.

In some embodiments, the identifier encodes a unique predetermined value selected from the set $\{1, \ldots, 1024\}$, selected from the set $\{1, \ldots, 4096\}$, selected from the set $\{1, \ldots, 16384\}$, selected from the set $\{1, \ldots, 65536\}$, selected from the set $\{1, \ldots, 262144\}$, selected from the set $\{1, \ldots, 1048576\}$, selected from the set $\{1, \ldots, 4194304\}$, selected from the set $\{1, \ldots, 16777216\}$, selected from the set $\{1, \ldots, 67108864\}$, or selected from the set $\{1, \ldots, 1 \times 10^{12}\}$.

In some embodiments, the convergence criterion is that the adjusting fails to change the initial assumption of (i) the number of components that contribute to each pool of measurement string samplings that includes measurement string samplings that map to components that overlap the first position or the second position and (ii) the class assignment of the measurement string samplings that map onto components that overlap the first position or the second position using the calculated basis of the sequence event arising between the first position and the second position in the first string or the second string from each of the plurality of models from a prior instance of the calculating (C).

In some embodiments, the plurality of components comprises ten thousand components or one hundred thousand components.

In some embodiments, the method further comprises repeating the identifying, calculating, adjusting, and repeating for each different pair of first and second positions in the ground truth string in a plurality of different pairs of first and second positions in the ground truth string. In some such embodiments, the plurality of different pairs of first and second positions in the ground truth string comprises 100 or more different pairs of first and second positions in the ground truth string. In some such embodiments, the plurality of different pairs of first and second positions in the ground truth string comprises 10000 or more different pairs of first and second positions in the ground truth string.

In some embodiments, the one or more processors each have a clock cycle of greater than one gigahertz and the obtaining, identifying, calculating, adjusting and repeating take more than two seconds to be executed by the one or more processors.

In some embodiments, the one or more processors each have a clock cycle of greater than two gigahertz and the obtaining, identifying, calculating, adjusting and repeating take more than five seconds to be executed by the one or more processors.

Another aspect of the present disclosure provides a non-transitory computer readable storage medium storing one or more programs configured for execution by a computer. The one or more programs comprising instructions determine the integrity of a first string and a second string with respect to a ground truth string through a two phase method. The ground truth string corresponds to an entirety of the first string and an entirety of the second string. The first string and the second string are not fully determined. The two phase method comprises obtaining a construct that represents a plurality of components. Each respective component in the plurality of components maps to a different contiguous portion of the ground truth string and represents less than one percent of the ground truth string. The construct comprises a plurality of measurement string sampling pools. Each measurement string sampling pool is (i) characterized by a different identifier in a plurality of identifiers and (ii) comprises a corresponding plurality of measurement string samplings. Each respective measurement string sampling in the corresponding plurality of measurement string samplings of a measurement string sampling pool in the plurality of measurement string sampling pools (i) is obtained from an optical measurement device and (ii) includes the same identifier string in addition to a coding string that consists of a portion of the first string or the second string. Each respective measurement string sampling in the plurality of measurement string samplings of a measurement string sampling pool in the plurality of measurement string sampling pools is assigned to (i) a first class when the coding region of the respective measurement string sampling matches a portion of the first string, (ii) a second class when the coding region of the respective sampling matches a portion of the second string or (iii) a third class when the coding region of the respective measurement string sampling matches the portion of the first string as well as the portion of the second string.

The plurality of measurement string samplings across each respective measurement string sampling pool in the plurality of measurement string sampling pools collectively forms a Poisson or near Poisson distribution of measurement string samplings across both the first string and the second string.

At least some of the measurement string samplings in the plurality of measurement string sampling pools have not been assigned to the first class, the second class, or the third class with absolute certainty. Each plurality of measurement string samplings represents a single corresponding component in the plurality of components or two discrete corresponding components in the plurality of components. The data construct does not include measurement string samplings for at least a predetermined portion of each component in the plurality of components.

The method continues by identifying a first position in the ground truth string and a second position in the ground truth string. There is calculated, as part of a first phase of the two phase method, an initial basis of a sequence event arising between the first position and the second position in the first string or the second string using each of a plurality of models and an initial assumption of (i) the number of components that contribute to each pool of measurement string samplings that includes measurement string samplings that collectively encompass the first position or the second position and (ii) the class assignment of the measurement string samplings that map onto components that overlap the first position or the second position, wherein each model in the plurality of models posits an observed distribution of measurement string samplings in the construct across the portion of the ground truth string that is bounded by the first position and the second position against an expected distribution of measurement string samplings in the construct across the ground truth string upon introduction of a sequence event. A first model in the plurality of models assumes that no sequence event occurs between the first position and the second position in the first string or the second string. A second model in the plurality of models assumes that a sequence event occurs between the first position and the second position in both the first string and the second string. A third model in the plurality of models assumes that a sequence event occurs between the first position and the second position in only one of the first string and the second string but not the other of the first string and the second string.

The method continues by adjusting, as part of the second phase of the two phase method, the initial assumption of (i) the number of components that contribute to each pool of measurement string samplings that includes measurement string samplings that map to components that overlap the first position or the second position and (ii) the class assignment of the measurement string samplings that map onto components that overlap the first position or the second position using the calculated basis of the sequence event arising between the first position and the second position in the first string or the second string from each of the plurality of models.

This calculating and adjusting is repeated until a convergence criterion is satisfied thereby determining the integrity of a first string and the second string with respect to the ground truth string.

Another aspect of the present disclosure provides a method of determining the integrity of a first string and a second string with respect to a ground truth string through a two phased method. In this aspect of the present disclosure, the ground truth string corresponds to an entirety of the first string and an entirety of the second string. The first string is not fully determined. The second string is not fully determined. Further, the two phased method comprises obtaining a construct that represents a plurality of components. Each respective component in the plurality of components maps to a different contiguous portion of the ground truth string and represents less than one percent of the ground truth string. The construct comprises a plurality of measurement string sampling pools. Each measurement string sampling pool is (i) characterized by a different identifier in a plurality of identifiers and (ii) comprises a corresponding plurality of measurement string samplings. Each respective measurement string sampling in the corresponding plurality of measurement string samplings of a measurement string sampling pool in the plurality of measurement string sampling pools (i) is obtained from an optical measurement device and (ii) includes the same identifier string in addition to a coding string that consists of a portion of the first string or the second string. Each respective measurement string sampling in the plurality of measurement string samplings of a measurement string sampling pool in the plurality of measurement string sampling pools is assigned to (i) a first class when the coding region of the respective measurement string sampling matches a portion of the first string, (ii) a second class when the coding region of the respective sampling matches a portion of the second string or (iii) a third class when the coding region of the respective measurement string sampling matches the portion of the first string as well as the portion of the second string. The plurality of measurement string samplings across each respective measurement string sampling pool in the plurality of measurement string sampling pools collectively forms a Poisson or near Poisson distribution of measurement string samplings across both the first string and the second string. At least some of the measurement string samplings in the plurality of measurement string sampling pools have not been assigned to the first class, the second class, or the third class with absolute certainty. Each plurality of measurement string samplings represents a single corresponding component in the plurality of components or two discrete corresponding components in the plurality of components. The data construct does not include measurement string samplings for at least a predetermined portion of each component in the plurality of components.

A first position in the ground truth string and a second position in the ground truth string are identified and there is calculated, as part of a first phase of the two phased method, an initial basis of a sequence event arising between the first position and the second position in the first string or the second string using each of a plurality of models and an initial assumption of (i) the number of components that contribute to each pool of measurement string samplings that includes measurement string samplings that collectively encompass the first position or the second position and (ii) the class assignment of the measurement string samplings that map onto components that overlap the first position or the second position, wherein each model in the plurality of models posits an observed distribution of measurement string samplings in the construct across the portion of the ground truth string that is bounded by the first position and the second position against an expected distribution of measurement string samplings in the construct across the ground truth string upon introduction of a sequence event. A first model in the plurality of models assumes that no sequence event occurs between the first position and the second position in the first string or the second string. A second model in the plurality of models assumes that a sequence event occurs between the first position and the second position in both the first string and the second string. A third model in the plurality of models assumes that a sequence event occurs between the first position and the second position in only one of the first string and the second string but not the other of the first string and the second string.

The method continues by adjusting, as part of a second phase of the two phased method, the initial assumption of (i) the number of components that contribute to each pool of measurement string samplings that includes measurement string samplings that map to components that overlap the first position or the second position and (ii) the class assignment of the measurement string samplings that map onto components that overlap the first position or the second position using the calculated basis of the sequence event arising between the first position and the second position in the first string or the second string from each of the plurality of models.

The calculating and adjusting are repeated until a convergence criterion is satisfied thereby determining the integrity of a first string and the second string with respect to the ground truth string.

Thus, these methods, systems, and non-transitory computer readable storage medium provide improved methods for determining the integrity of a first query string and a second query string with respect to a ground truth string through a two phase method such as an expectation-maximization method.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

BRIEF DESCRIPTION OF THE DRAWINGS

The implementations disclosed herein are illustrated by way of example, and not by way of limitation, in the figures of the accompanying drawings. Like reference numerals refer to corresponding parts throughout the drawings. In the figures that include method flowcharts, boxes that are dashed indicate example embodiments.

FIG. 3 illustrates the relationship between the test nucleic acid (e.g., chromosomal DNA), the different molecules (fragments) of the larger test nucleic acid, and sequence reads of molecules (fragments) in accordance with some embodiments.

FIGS. 4A, 4B, 4C, 4D, 4E, 4F, 4G and 4H illustrate exemplary data in accordance with some embodiments.

FIG. 7A illustrates the distribution of sequencing reads about locus positions x and y when there is no structural variation arising between positions x and y in accordance with some embodiments of the present disclosure.

FIG. 7B illustrates the distribution of sequencing reads about locus positions x and y when there is a deletion arising between positions x and y in accordance with some embodiments of the present disclosure.

FIG. 7C illustrates the distribution of sequencing reads about locus positions x and y when there is an inversion arising between positions x and y in accordance with some embodiments of the present disclosure.

DETAILED DESCRIPTION

The present disclosure generally provides methods, processes, and particularly computer implemented processes and non-transistory computer program products for use in determining the integrity of a first string and a second string with respect to a ground truth string through a two phase method. In particular, the first and second strings are analyzed for structural variations (e.g., deletions, duplications, copy-number variants, insertions, inversions, translocations, long term repeats (LTRs), short term repeats (STRs), and a variety of other useful characterizations) relative to the ground truth string. Details of implementations are now described in relation to the Figures.

Figure 1:
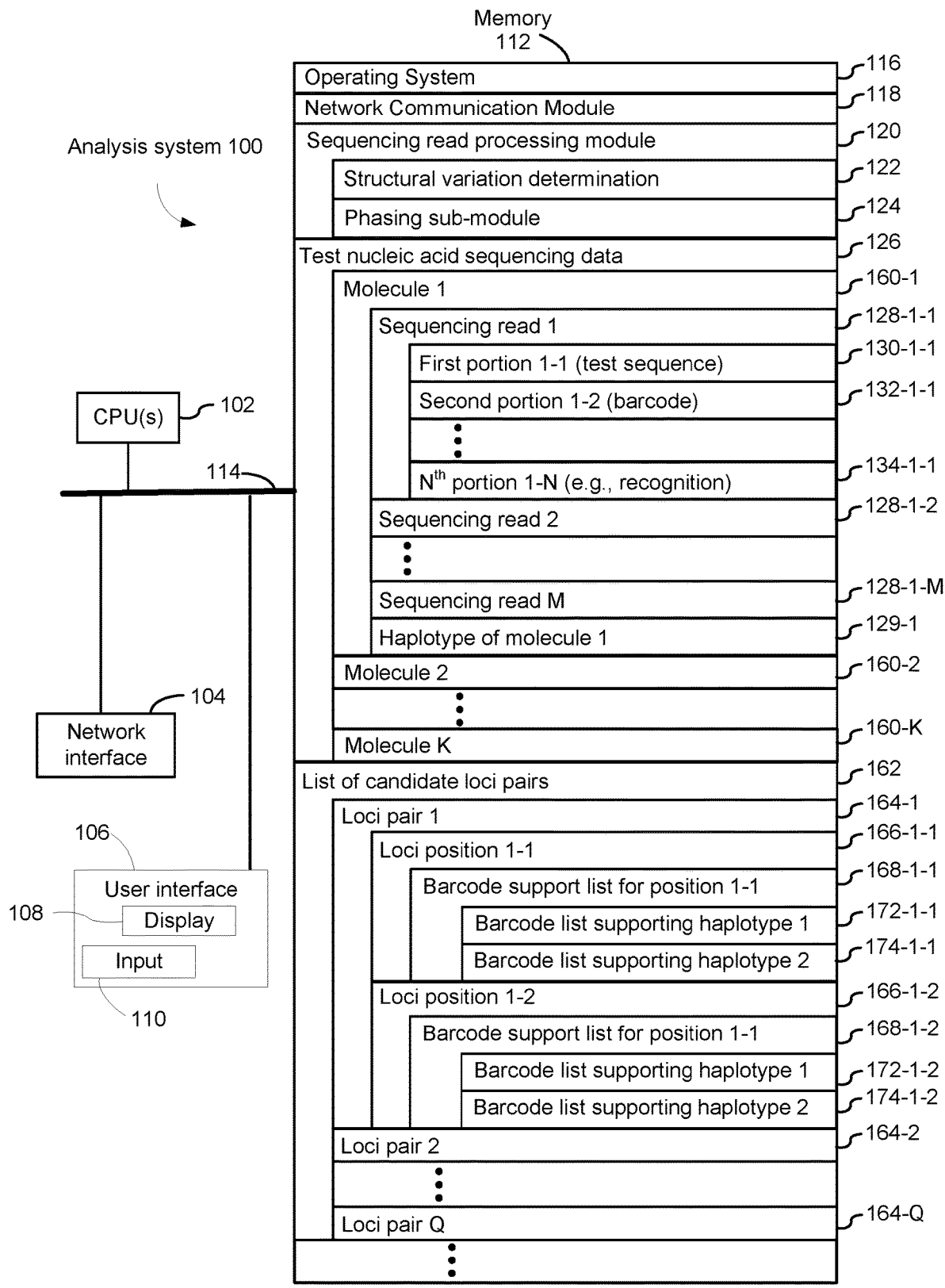
FIG. 1 is an example block diagram illustrating a computing device in accordance with some implementations.

FIG. 1 is a block diagram illustrating an analysis system 100 in accordance with some implementations. The device 100 in some implementations includes one or more processing units CPU(s) 102 (also referred to as processors), one or more network interfaces 104, a user interface 106, a memory 112, and one or more communication buses 114 for interconnecting these components. The communication buses 114 optionally include circuitry (sometimes called a chipset) that interconnects and controls communications between system components. The memory 112 typically includes high-speed random access memory, such as DRAM, SRAM, DDR RAM, ROM, EEPROM, flash memory, CD-ROM, digital versatile disks (DVD) or other optical storage, magnetic cassettes, magnetic tape, magnetic disk storage or other magnetic storage devices, other random access solid state memory devices, or any other medium which can be used to store desired information; and optionally includes non-volatile memory, such as one or more magnetic disk storage devices, optical disk storage devices, flash memory devices, or other non-volatile solid state storage devices. The memory 112 optionally includes one or more storage devices remotely located from the CPU(s) 102. The memory 112, or alternatively the non-volatile memory device(s) within the memory 112, comprises a non-transitory computer readable storage medium. In some implementations, the memory 112 or alternatively the non-transitory computer readable storage medium stores the following programs, modules and data structures, or a subset thereof:

- an optional operating system 116, which includes procedures for handling various basic system services and for performing hardware dependent tasks;
- an optional network communication module (or instructions) 118 for connecting the device 100 with other devices, or a communication network;
- an optional sequence read processing module 120 for processing sequence reads, including a structural variation determination sub-module 122 for identifying structural variations in a genetic sample from a single organism of a species and a phasing sub-module 124 for identifying the haplotype of each sequence read of the genetic sample;
- one or more nucleic acid sequencing datasets 126, each such dataset obtained using a genetic sample from a single organism of a species and comprising, for each molecule 160 in a plurality of molecules, a number of sequencing reads 128 for the molecule and the haplotype of the molecule 129, each sequencing 128 including a first portion 130 that is a portion of a test sequence and a second portion 132 that is a unique barcode 132; and
- a list of candidate loci pairs 162, each such loci pair 164 in the list of candidate loci pairs including a first loci position 166 and a second loci position 166, the first loci position including a barcode support list 168 that itself comprises a barcode list 172 supporting a first haplotype at the first loci position and a barcode list 174 supporting a second haplotype at the first loci position, the second loci position including another barcode support list 168 that itself comprises a barcode list 172 supporting a first haplotype at the second loci position and a barcode list 174 supporting a second haplotype at the second loci position.

In some implementations, the user interface 106 includes an input device (e.g., a keyboard, a mouse, a touchpad, a track pad, and/or a touch screen) 100 for a user to interact with the system 100 and a display 108.

In some implementations, one or more of the above identified elements are stored in one or more of the previously mentioned memory devices, and correspond to a set of instructions for performing a function described above. The above identified modules or programs (e.g., sets of instructions) need not be implemented as separate software programs, procedures or modules, and thus various subsets of these modules may be combined or otherwise re-arranged in various implementations. In some implementations, the memory 112 optionally stores a subset of the modules and data structures identified above. Furthermore, in some embodiments, the memory stores additional modules and data structures not described above. In some embodiments, one or more of the above identified elements is stored in a computer system, other than that of system 100, that is addressable by system 100 so that system 100 may retrieve all or a portion of such data when needed.

Although FIG. 1 shows an "analysis system 100," the figure is intended more as functional description of the various features which may be present in computer systems than as a structural schematic of the implementations described herein. In practice, and as recognized by those of ordinary skill in the art, items shown separately could be combined and some items could be separated.

FIG. 2 is a flow chart illustrating a method for determining the integrity of a first string and a second string with respect to a ground truth string through a two phase method (202).

An example of a "ground truth string" is the human genome. In the present disclosure, an example of a first query sequence is a first haplotype of a human genome of a test subject. In the present disclosure, an example of a second query sequence is a second haplotype of a human genome of the same test subject.

In the present disclosure, the terms "component" and "molecule 160" are used interchangeably.

In the present disclosure, the term "measurement string sampling pool" refers to sequence reads 128 with the same barcode 132.

In the present disclosure, the terms "measurement string sampling," "sequence read," and "sequencing read" are used interchangeably.

In the present disclosure, the terms "construct" and "test nucleic acid sequencing dataset" are used interchangeably.

In the present disclosure, the terms "first class" and "heterozygous for haplotype 1" are used interchangeably.

In the present disclosure, the terms "second class" and "heterozygous for haplotype 2" are used interchangeably.

In the present disclosure, the terms "third class" and "homozygous" are used interchangeably.

In the present disclosure, the terms "barcode," "bar code," and "identifier" are used interchangeably.

In some embodiments, the method takes place at a computer system having one or more processors, and memory storing one or more programs for execution by the one or more processors in accordance with some embodiments (204).

Obtaining a plurality of sequence reads. In accordance with the disclosed systems and methods, a construct that represents a plurality of components, where each respective component in the plurality of components maps to a different contiguous portion of the ground truth string and represents less than one percent of the ground truth string, is obtained. The construct comprises a plurality of measurement string sampling pools.

Each measurement string sampling pool is (i) characterized by a different identifier in a plurality of identifiers and (ii) comprises a corresponding plurality of measurement string samplings. Each respective measurement string sampling in the corresponding plurality of measurement string samplings of a measurement string sampling pool in the plurality of measurement string sampling pools (i) is obtained from an optical measurement device and (ii) includes the same identifier string in addition to a coding string that consists of a portion of the first string or the second string. Thus, referring to FIG. 1, in some embodiments, each measurement string sampling is a sequencing read 128 comprising s first portion 130 that encodes a portion of a sequence from a subject and a second portion 132 that is a unique barcode 132.

In some embodiments, a plurality of sequence reads 128 is obtained using a test nucleic acid from a subject. In typical embodiments the subject is a human subject. In some embodiments, the subject is a mammalian subject. In some embodiments, the subject is a diploid subject. As such, because the subject is diploid their genome constitutes a first string of a first haplotype, and a second string of a second haplotype. A ground truth string, such as a reference genome corresponds to an entirety of the first string and an entirety of the second string. An example ground truth string, in the form of the human genome, is disclosed in Abecasis et al., 2012, "An integrated map of genetic variation from 1,092 human genomes," Nature. 491 (7422): 56-65, which is hereby incorporated by reference. The correspondence between the ground truth string and the first and second string is not an exact correspondence. For instance, there are significant differences among the genomes of human individuals (on the order of 0.1%). See Abecasis, id. As such, in some embodiments the first string and the second string may each differ with respect to the ground truth string by as much as 1 percent of their respective sequences, or as much as 0.5 percent of their respective sequences, or by as much as much as 0.2 percent of their respective sequences and still correspond to each other. For instance, a number of single nucleotide polymorphisms (SNPs) may exist between the first string and the ground truth string, between the second string and the ground truth string, and between the first string and the second string. In some embodiments, there exist deletions, duplications, copy-number variants, insertions, inversions, translocations, long term repeats (LTRs), short term repeats (STRs), and a variety of other structural variations between the first string, the second string and the ground truth string.

In some embodiments, the ground truth string is a reference human genome for a species, such as human. As such, in some embodiments, the ground truth string includes the nucleic acid sequence of all the chromosomes of a reference human subject.

In some embodiments, the first string and the second string are each from a single test subject, such a human subject in need of diagnosis or genetic analysis. In such embodiments, the first string is the first haplotype of the test subject across one parental copy of the chromosomes for the test subject and the second string is the second haplotype of the test subject across the other parental copy of the chromosomes for the test subject. As such, the first string and the second string collectively constitute a test nucleic acid of a subject.

In some embodiments, the first string and the second string are each from a single test subject, such a human subject in need of diagnosis or genetic analysis. In such embodiments, the first string is the first haplotype of the test subject across the genome of the test subject and the second string is the second haplotype of the test subject across the genome of the test subject. As such, the first string and the second string collectively constitute a test nucleic acid of a subject.

In some embodiments, the first string and the second string are each from a single test subject, such a human subject in need of diagnosis or genetic analysis. In such embodiments, the first string is the genetic sequence of one set of chromosomes across the genome of the test subject and the second string is the genetic sequence of the other set of chromosomes across the genome of the test subject. As such, the first string and the second string collectively constitute a test nucleic acid of a subject. For instance, in humans, there are 23 pairs of chromosomes. In some such embodiments, the first string is the genetic sequence of one copy of each of the chromosomes in the set of 23 chromosome pairs across the genome of the test subject and the second string is the genetic sequence of the other copy of each of the chromosomes in the set of 23 chromosome pairs across the genome of the test subject.

In some embodiments, the first string and the second string only represent a portion of the genome of a test subject. For example, in some embodiments, in some embodiments the first string is the genetic sequence of one copy a single first chromosome in a first chromosome pair in the set of 23 chromosome pairs and the second string is the genetic sequence of a single second chromosome in the first chromosome pair.

The sequence reads are obtained to elucidate the aforementioned structural variations in accordance with the systems and methods of the present disclosure. Such sequence reads ultimately form the basis of the test nucleic acid sequencing dataset 126 of FIG. 1, which is also termed in the present disclosure a "construct." As illustrated in FIG. 1, each respective sequence read 128 in the plurality of sequence reads comprises a first portion 130 that corresponds to a subset of the test nucleic acid and a second portion 132 that encodes a barcode for the respective sequence read. The barcode is independent of the sequencing data of the test nucleic acid. In other words, the barcode is not derived from, or a function of the sequencing data of the test nucleic acid. In some instances a sequence read is referred to herein as a next generation sequencing (NGS) read-pair.

In some embodiments, a first sequence read in the plurality of sequence reads corresponds to a subset of the test nucleic acid that is 2×36 bp, 2×50 bp, 2×76 bp, 2×100 bp, 2×150 bp or 2×250 bp, where the terminology 2×N bp means that the sequence read has two reads of length N base pairs from a single nucleic acid (e.g., from a test nucleic acid obtained from a biological sample) that are separated by an unspecified length. In some embodiments this unspecified length is between 200 to 1200 base pairs. In some embodiments, a first sequence read in the plurality of sequence reads represents at least 25 bp, at least 30 bp, at least 50 bp, at least 100 bp, at least 200 bp, at least 250 bp, at least 500 bp, less than 500 bp, less than 400 bp, or less than 300 bp of a single piece of nucleic acid (e.g., from a test nucleic acid obtained from a biological sample).

More generally, sequence reads 128 obtained in some embodiments are assembled into contigs with an N50 of at least about 10 kbp, at least about 20 kbp, or at least about 50 kbp. In more preferred aspects, sequence reads are assembled into contigs of at least about 100 kbp, at least about 150 kbp, at least about 200 kbp, and in many cases, at least about 250 kbp, at least about 300 kbp, at least about 350 kbp, at least about 400 kbp, and in some cases, or at least about 500 kbp or more. In still other embodiments, sequence reads are phased into contigs with an N50 in excess of 200 kbp, in excess of 300 kbp, in excess of 400 kbp, in excess of 500 kbp, in excess of 1 Mb, or even in excess of 2 Mb are obtained in accordance with the present disclosure. See Miller et al., 2010, "Assembly algorithms for next generation sequencing data," Genomics 95, pp. 315-327, which is hereby incorporated by reference for a definition on N50 and conventional contig assembly algorithms.

In some embodiments, as illustrated in FIG. 3, to obtain the plurality of sequence reads 128, a larger contiguous nucleic acid 302 (the test nucleic acid, e.g., chromosomal DNA) is fragmented to form molecules 160 and these molecules are compartmentalized, or partitioned into discrete compartments or partitions (referred to interchangeably herein as partitions). In some embodiments, the contiguous nucleic acid 302 includes the first string and the second string under study (e.g., with the first string representing the sequence of one copy of chromosomes and the other second string representing the sequence of the other copy of chromosomes of a diploid test subject).

In some embodiments, the test nucleic acid 602 is the genome of a multi-chromosomal organism such as a human. In some embodiments, more than 10, more than 100, more than 1000, more than 10,000, more than 100,000, more than $1 \times 10^6$, or more than $5 \times 10^6$ sets of sequence reads are obtained, corresponding more than 10, more than 100, more than 1000, more than 10,000, more than 100,000, more than $1 \times 10^6$, or more than $5 \times 10^6$ partitions.

FIG. 3 thus illustrates the relationship between the larger contiguous nucleic acid 602, the different molecules 160 (fragments) of the larger contiguous nucleic acid, and sequence reads 128 of fragments. Typically, between 1 and 100 molecules 160, between 2 and 50 molecules 160 or between 3 and 25 molecules 160 are each partitioned into a separate partition. In any event, sufficiently few of the fragments 704 are partitioned into the same partition such that the chance that the fragments 704 in a single partition have any appreciable overlapping sequences is unlikely.

Sequence reads 128 of each molecule 160 are made. In typical embodiments, sequence reads 128 are short in length (e.g., less than 1000 bases) so that they can be sequenced in automated sequencers. Each sequence read 128 in a partition includes a common second portion 132 that forms a barcode that is independent of the sequence of the larger contiguous nucleic 602 acid nucleic acid and that identifies the partition, in a plurality of partitions, in which the respective sequence read was formed.

In some embodiments, the test nucleic acid is the genome of a multi-chromosomal organism such as a human. In some embodiments, the biological sample is from a multi-chromosomal species and the test nucleic acid comprises a plurality of nucleic acids collectively representing a plurality of chromosomes from the multi-chromosomal species.

Each partition maintains separation of its own contents from the contents of other partitions. As used herein, the partitions refer to containers or vessels that may include a variety of different forms, e.g., wells, tubes, micro or nanowells, through holes, or the like. In preferred aspects, however, the partitions are flowable within fluid streams. In some embodiments, these vessels are comprised of, e.g., microcapsules or micro-vesicles that have an outer barrier surrounding an inner fluid center or core, or have a porous matrix that is capable of entraining and/or retaining materials within its matrix. In some embodiments, however, these partitions comprise droplets of aqueous fluid within a non-aqueous continuous phase, e.g., an oil phase. A variety of different suitable vessels are described in, for example, U.S. Patent Publication No. 2014/0155295 A1, published Jun. 5, 2014, which is hereby incorporated by reference herein in its entirety. Likewise, emulsion systems for creating stable droplets in non-aqueous or oil continuous phases are described in detail in, e.g., Published U.S. Patent Application No. 2010-0105112, which is hereby incorporated by reference herein in its entirety. In certain embodiments, microfluidic channel networks are particularly suited for generating partitions. Examples of such microfluidic devices include those described in detail in Provisional U.S. Patent Application No. 61/977,804, filed Apr. 4, 2014, as well as U.S. Pat. No. 9,694,361 entitled "Fluidic Devices, Systems, and Methods for Encapsulating and Partitioning Reagents, and Applications of Same, which is hereby incorporated by reference in its entirety for all purposes. Alternative mechanisms may also be employed in the partitioning of individual cells, including porous membranes through which aqueous mixtures of cells are extruded into non-aqueous fluids. Such systems are generally available from, e.g., Nanomi, Inc.

In the case of droplets in an emulsion, partitioning of the test nucleic acid molecules 160 into discrete partitions may generally be accomplished by flowing an aqueous, sample containing stream, into a junction into which is also flowing a non-aqueous stream of partitioning fluid, e.g., a fluorinated oil, such that aqueous droplets are created within the flowing stream partitioning fluid, where such droplets include the sample materials. As described below, the partitions, e.g., droplets, also typically include co-partitioned barcode oligonucleotides.

The relative amount of sample materials within any particular partition may be adjusted by controlling a variety of different parameters of the system, including, for example, the concentration of test nucleic acid fragments in the aqueous stream, the flow rate of the aqueous stream and/or the non-aqueous stream, and the like. The partitions described herein are often characterized by having overall volumes that are less than 1000 pL, less than 900 pL, less than 800 pL, less than 700 pL, less than 600 pL, less than 500 pL, less than 400 pL, less than 300 pL, less than 200 pL, less than 100 pL, less than 50 pL, less than 20 pL, less than 10 pL, or even less than 1 pL. Where co-partitioned with beads, it will be appreciated that the sample fluid volume within the partitions may be less than 90% of the above described volumes, less than 80%, less than 70%, less than 60%, less than 50%, less than 40%, less than 30%, less than 20%, or even less than 10% of the above described volumes. In some cases, the use of low reaction volume partitions is particularly advantageous in performing reactions with small amounts of starting reagents, e.g., input test nucleic acid fragments. Methods and systems for analyzing samples with low input nucleic acids are presented in U.S. Provisional Patent Application No. 62/017,580, filed Jun. 26, 2014, as well as United States Patent Publication No. 2015-0376605 A1, published Dec. 31, 2015 and entitled "Methods and Compositions for Sample Analysis," the full disclosure of which is hereby incorporated by reference in its entirety.

Once the molecules 160 are introduced into their respective partitions, the molecules 160 within partitions are generally provided with unique barcodes such that, upon characterization of those molecules 160, may be attributed as having been derived from their respective partitions. In some embodiments, such unique barcodes are previously, subsequently or concurrently delivered to the partitions that hold the compartmentalized or partitioned molecules 160, in order to allow for the later attribution of the characteristics, e.g., nucleic acid sequence information, to the sample nucleic acids included within a particular compartment (partition), and particularly to relatively long stretches of contiguous sample nucleic acids that may be originally deposited into the partitions.

Accordingly, the molecules 160 are typically co-partitioned with the unique barcodes (e.g., barcode sequences). In particularly preferred aspects, the unique barcodes are provided in the form of oligonucleotides that comprise nucleic acid barcode sequences that is attached to test nucleic acid molecules in the partitions. The oligonucleotides are partitioned such that as between oligonucleotides in a given partition, the nucleic acid barcode sequences contained therein are the same, but as between different partitions, the oligonucleotides can, and preferably have differing barcode sequences. In preferred embodiments, only one nucleic acid barcode sequence is associated with a given partition, although in some embodiments, two or more different barcode sequences are present in a given partition.

The nucleic acid barcode sequences will typically include from 6 to about 20 or more nucleotides within the sequence of the oligonucleotides. In some embodiments, these nucleotides are completely contiguous, i.e., in a single stretch of adjacent nucleotides. In alternative embodiments, they are separated into two or more separate subsequences that are separated by one or more nucleotides. Typically, separated subsequences are separated by about 4 to about 16 intervening nucleotides.

The test nucleic acid 302 is typically partitioned such that the nucleic acids are present in the partitions in relatively long fragments or stretches of contiguous nucleic acid molecules 160 of the original test nucleic acid 302. Referring to FIG. 3, these molecules 160 typically represent a number of overlapping fragments of the overall test nucleic acid to be analyzed, e.g., an entire chromosome, exome, or other large genomic fragment (e.g., the first string and the second string). In some embodiments, the test nucleic acid 302 (first string and second string) includes whole genomes, individual chromosomes, exomes, amplicons, or any of a variety of different nucleic acids of interest. Typically, the molecules 160 of the test nucleic acid 302 that are partitioned are longer than 1 kbp, longer than 5 kbp, longer than 10 kbp, longer than 15 kbp, longer than 20 kbp, longer than 30 kbp, longer than 40 kbp, longer than 50 kbp, longer than 60 kbp, longer than 70 kbp, longer than 80 kbp, longer than 90 kbp or even longer than 100 kbp.

The test nucleic acid 302 (comprising the first string and the second string of a diploid genome of a single test subject) is also typically partitioned at a level whereby a given partition has a very low probability of including two molecules 160 of the starting test nucleic acid 302. This is typically accomplished by providing the test nucleic acid 302 at a low input amount and/or concentration during the partitioning process. As a result, in preferred cases, a given partition includes a number of long, but non-overlapping molecules 160 of the starting test nucleic acid 302. The nucleic acid molecules 160 in the different partitions are then associated with unique barcodes where, for any given partition, nucleic acids contained therein possess the same unique barcode, but where different partitions include different unique barcodes. Moreover, because the partitioning step allocates the sample components into very small volume partitions or droplets, it will be appreciated that in order to achieve the desired allocation as set forth above, one need not conduct substantial dilution of the sample, as would be required in higher volume processes, e.g., in tubes, or wells of a multi-well plate. Further, because the systems described herein employ such high levels of barcode diversity, one can allocate diverse barcodes among higher numbers of genomic equivalents, as provided above. In some embodiments, in excess of 10,000, 100,000, 500,000, etc. diverse barcode types are used to achieve genome:(barcode type) ratios that are on the order of 1:50 or less, 1:100 or less, 1:1000 or less, or even smaller ratios, while also allowing for loading higher numbers of genomes (e.g., on the order of greater than 100 genomes per assay, greater than 500 genomes per assay, 1000 genomes per assay, or even more) while still providing for far improved barcode diversity per genome. Here, each such genome is an example of a test nucleic acid.

Figure 4A:
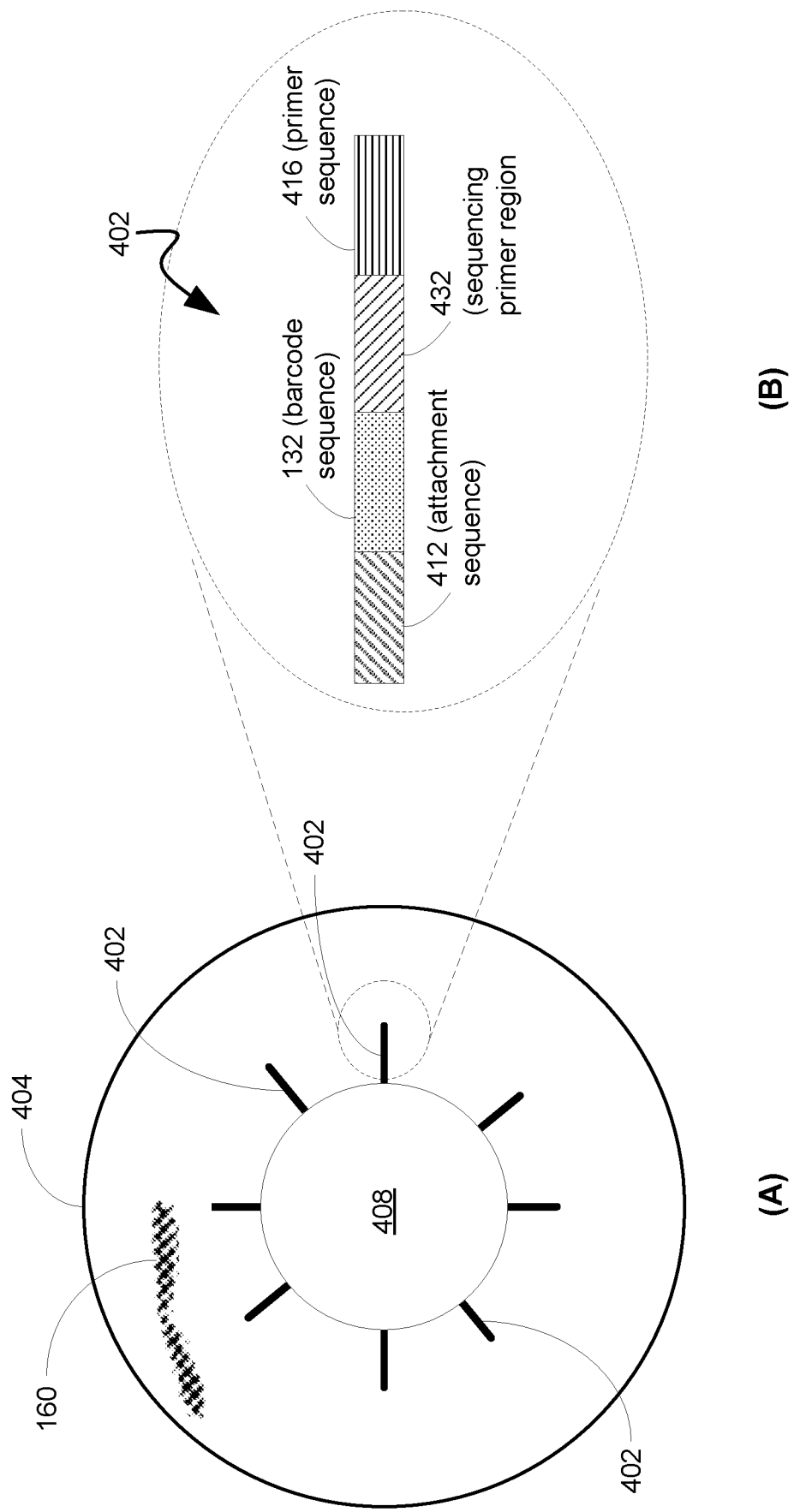

Referring to FIG. 4A, panel B, often the above-described partitioning is performed by combining the sample containing the test nucleic acid with a set of oligonucleotide tags 402 (containing the barcodes 132) that are releasably-attached to beads 408 prior to the partitioning step. The oligonucleotides 402 may comprise at least a primer region 416 and a barcode 132 region. Between oligonucleotides 402 within a given partition, the barcode region 132 is substantially the same barcode sequence, but as between different partitions, the barcode region in most cases is a different barcode sequence. In some embodiments, the primer region 416 is an N-mer (either a random N-mer or an N-mer designed to target a particular sequence) that is used to prime the molecules 160 within the sample within the partitions. In some cases, where the N-mer is designed to target a particular sequence, the primer region 416 is designed to target a particular chromosome (e.g., human chromosome 1, 2, 3, 4, 5, 6, 7, 8, 9, 10, 11, 12, 13, 14, 15, 16, 17, 18, 19, 20, 21, 22, X, or Y), or region of a chromosome, e.g., an exome or other targeted region. In some cases, the N-mer is designed to target a particular gene or genetic region, such as a gene or region associated with a disease or disorder (e.g., cancer). In some cases, the N-mer is designed to target a particular structural variation. Within the partitions, an amplification reaction is conducted using the primer sequence 416 (e.g. N-mer) to prime the molecule 160 that is a portion of the test nucleic acid fragments 302 (e.g., at different places along the length of the molecule 160). As a result of the amplification, each partition contains amplified products of the molecule 160 that is a portion of the test nucleic acid 302 that are attached to an identical or near-identical barcode, and that represent overlapping, smaller fragments of the nucleic acids in each partition. The barcode 132 therefore serves as a marker that signifies that a set of nucleic acids originated from the same partition, and thus potentially also originated from the same molecule 160 that is, in turn, a fragment of the test nucleic acid 302. It will be appreciated that there are typically molecules 160 in any given partition. Nevertheless, in typical embodiments, molecules 160 that are in the same partition typically do not have any significant overlap and so it is possible to localize the amplified sequence reads to the molecule 160 in any given partition. Following amplification, the amplified nucleic acids are pooled, sequenced to form sequence reads, and aligned using a sequencing algorithm. Because shorter sequence reads may, by virtue of their associated barcode sequences, be aligned and attributed to a single, long originating molecule 160 of the test nucleic acid 602, all of the identified variants on that sequence can be attributed to a single originating molecule 160 and single originating chromosome of the test nucleic acid 602. Further, by aligning multiple co-located variants across multiple molecules 160, one can further characterize that chromosomal contribution. Accordingly, conclusions regarding the phasing of particular genetic variants may then be drawn. Such information may be useful for identifying haplotypes, which are generally a specified set of genetic variants that reside on the same nucleic acid strand or on different nucleic acid strands. Moreover, additionally or alternatively, structural variants are identified.

In some embodiments, referring to FIG. 4A, the co-partitioned oligonucleotide tags 402 also comprise functional sequences in addition to the barcode sequence 132 and the primer region sequence 416. For instance, in some embodiments, the co-partitioned oligonucleotide tags 402 also comprise other functional sequences useful in the processing of the partitioned nucleic acids such as targeted or random/universal amplification primer sequences for amplifying molecules 160 within the partitions 404 while attaching the associated barcode sequences, sequencing primers, hybridization or probing sequences, e.g., for identification of presence of the sequences, or for pulling down barcoded nucleic acids, or any of a number of other potential functional sequences. See, for example, the disclosure on co-partitioning of oligonucleotides and associated barcodes and other functional sequences, along with sample materials as described in, for example, U.S. Patent Application Nos. 61/940,318, filed Feb. 7, 2014, 61/991,018, filed May 9, 2014, and U.S. patent application Ser. No. 14/316,383, filed on Jun. 26, 2014, as well as U.S. Pat. No. 9,644,204 entitled "Partitioning and Processing of Analytes and Other Species, the full disclosures of which is hereby incorporated by reference in their entireties.

In one exemplary process, beads are provided, where each such bead includes large numbers of the above described oligonucleotides releasably attached to the beads. In such embodiments, all of the oligonucleotides attached to a particular bead include the same nucleic acid barcode sequence, but a large number of diverse barcode sequences are represented across the population of beads used. Typically, the population of beads provides a diverse barcode sequence library that includes at least 1000 different barcode sequences, at least 10,000 different barcode sequences, at least 100,000 different barcode sequences, or in some cases, at least 1,000,000 different barcode sequences. Additionally, each bead typically is provided with large numbers of oligonucleotide molecules attached. In particular, the number of molecules of oligonucleotides including the barcode sequence on an individual bead may be at least about 10,000 oligonucleotides, at least 100,000 oligonucleotide molecules, at least 1,000,000 oligonucleotide molecules, at least 100,000,000 oligonucleotide molecules, and in some cases at least 1 billion oligonucleotide molecules.

In some embodiments, the oligonucleotides are releasable from the beads upon the application of a particular stimulus to the beads. In some cases, the stimulus is a photo-stimulus, e.g., through cleavage of a photo-labile linkage that may release the oligonucleotides. In some cases, a thermal stimulus is used, where elevation of the temperature of the beads environment results in cleavage of a linkage or other release of the oligonucleotides form the beads. In some cases, a chemical stimulus is used that cleaves a linkage of the oligonucleotides to the beads, or otherwise results in release of the oligonucleotides from the beads.

In some embodiments, the beads including the attached oligonucleotide tags 402 are co-partitioned with the individual samples, such that a single bead and a single sample are contained within an individual partition. In some cases, where single bead partitions are desired, it may be desirable to control the relative flow rates of the fluids such that, on average, the partitions contain less than one bead per partition, in order to ensure that those partitions that are occupied, are primarily singly occupied. Likewise, in some embodiments, the flow rate is controlled to provide that a higher percentage of partitions are occupied, e.g., allowing for only a small percentage of unoccupied partitions. In preferred aspects, the flows and channel architectures are controlled as to ensure a desired number of singly occupied partitions, less than a certain level of unoccupied partitions and less than a certain level of multiply occupied partitions.

FIG. 3 of U.S. Patent Application No. 62/072,214, filed Oct. 29, 2014, entitled "Analysis of Nucleic Acid Sequences," which is hereby incorporated by reference and the portions of the specification describing FIG. 3 provide a detailed example of one method for barcoding and subsequently sequencing a test nucleic acid (referred to in the reference as a "sample nucleic acid") in accordance with one embodiment of the present disclosure. As noted above, while single bead occupancy may be the most desired state, it will be appreciated that multiply occupied partitions, or unoccupied partitions may often be present. FIG. 4 of U.S. Patent Application No. 62/072,214, filed Oct. 29, 2014, entitled "Analysis of Nucleic Acid Sequences," which is hereby incorporated by reference and the portions of the specification describing FIG. 4 provide a detailed example of a microfluidic channel structure for co-partitioning samples and beads comprising barcode oligonucleotides in accordance with one embodiment of the present disclosure.

Once co-partitioned, the oligonucleotide tags 402 disposed upon the bead are used to barcode and amplify the partitioned samples. One process for use of these barcode oligonucleotides in amplifying and barcoding samples is described in detail in U.S. Patent Application Nos. 61/940,318, filed Feb. 7, 2014, 61/991,018, filed May 9, 2014, and Ser. No. 14/316,383, filed on Jun. 26, 2014, the full disclosures of which are hereby incorporated by reference in their entireties. Briefly, in one aspect, the oligonucleotides present on the beads that are co-partitioned with the samples are released from their beads into the partition with the samples. The oligonucleotides typically include, along with the barcode sequence 132, a primer sequence at its 5' end 416. In some embodiments, this primer sequence is a random oligonucleotide sequence intended to randomly prime numerous different regions of the samples. In some embodiments the primer sequence 416 is a specific primer sequence targeted to prime upstream of a specific targeted region of the sample.

Once released, the primer portion of the oligonucleotide anneals to a complementary region of molecules 160 in the partition. Extension reaction reagents, e.g., DNA polymerase, nucleoside triphosphates, co-factors (e.g., $Mg^{2+}$ or $Mn^{2+}$ etc.), that are also co-partitioned with the molecules 160 and beads 404, extend the primer sequence using the molecules 160 as a template, to produce a complementary sequence to a portion of the strand of the molecules 160 to which the primer annealed, and this complementary sequence includes the oligonucleotide 402 and its associated barcode sequence 132. Annealing and extension of multiple primers to different portions of the molecules 160 in the partition 404 may result in a large pool of overlapping complementary portions of the molecules 160, each possessing its own barcode sequence 132 indicative of the partition 404 in which it was created. In some cases, these complementary fragments may themselves be used as a template primed by the oligonucleotides present in the partition 404 to produce a complement of the complement that again, includes the barcode sequence 132. In some cases, this replication process is configured such that when the first complement is duplicated, it produces two complementary sequences at or near its termini, to allow the formation of a hairpin structure or partial hairpin structure that reduces the ability of the molecule to be the basis for producing further iterative copies. A schematic illustration of one example of this is shown in FIG. 4F.

As FIG. 4A shows, oligonucleotides 402 that include a barcode sequence 132 are co-partitioned in, e.g., a droplet 404 in an emulsion, along with a sample molecule 160. In some embodiments, the oligonucleotides 402 are provided on a bead 408 that is co-partitioned with the molecule 160. The oligonucleotides 402 are preferably releasable from the bead 408, as shown in FIG. 3A, panel (A). As shown in FIG. 4A panel (B), the oligonucleotides 402 includes a barcode sequence 132, in addition to one or more functional sequences, e.g., sequences 412, 432 and 416.

For example, oligonucleotide 402 is shown as further comprising attachment sequence 412 that may function as an attachment or immobilization sequence for a given sequencing system, e.g., a P5 sequence used for attachment in flow cells of an ILLUMINA, HISEQ or MISEQ system. In other words, attachment sequence 412 is used to reversibly attach oligonucleotide 402 to a bead 408 in some embodiments.

As shown in FIG. 4A, panel B, the oligonucleotide 402 also includes a primer sequence 416, which may include a random or targeted N-mer (discussed above) for priming replication of portions of the molecule 160.

Also included within exemplary oligonucleotide 402 of FIG. 4A, panel B, is a sequence 432 which may provide a sequencing priming region, such as a "read1" or R1 priming region, that is used to prime polymerase mediated, template directed sequencing by synthesis reactions in sequencing systems. In many cases, the barcode sequence 132, immobilization sequence 412 and exemplary R1 sequence 432 may be common to all of the oligonucleotides 302 attached to a given bead. The primer sequence 416 may vary for random N-mer primers, or may be common to the oligonucleotides on a given bead for certain targeted applications.

Figure 4B:
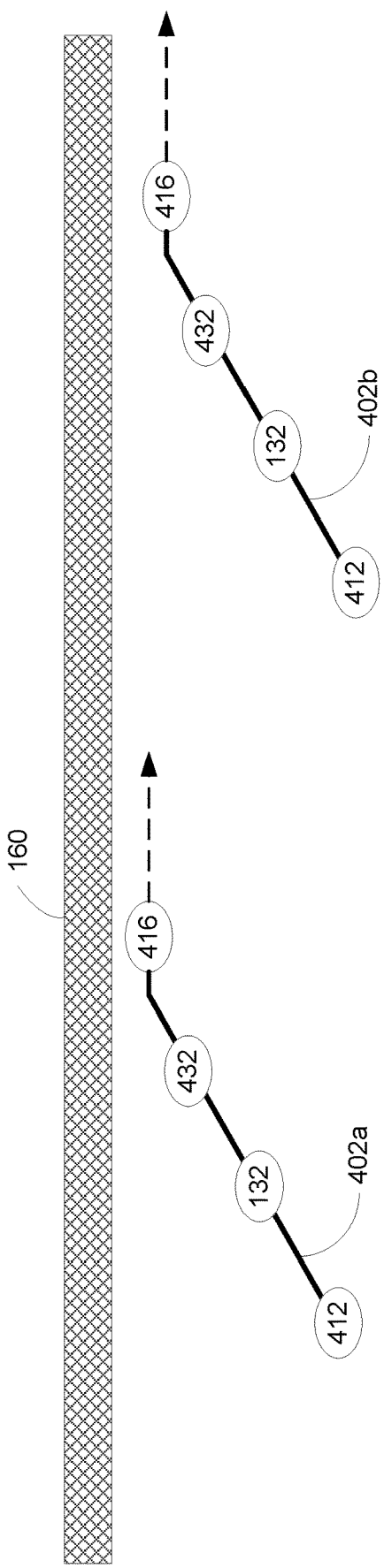

Referring to FIG. 4B, based upon the presence of primer sequence 416, the oligonucleotides 402a and 402b are able to prime the molecule 160, which allows for extension of the oligonucleotides 402a and 402b using polymerase enzymes and other extension reagents also co-portioned with the bead 504 and molecule 160.

Figure 4C:
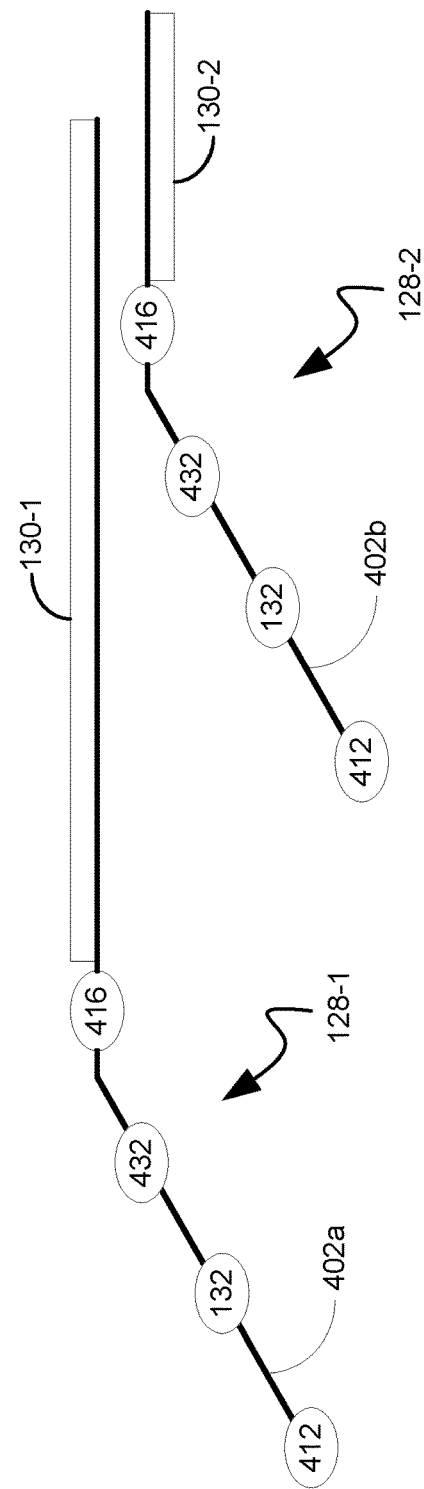

As shown in FIG. 4C, following extension of the oligonucleotides that, for random N-mer primers, would anneal to multiple different regions of the molecule 160, multiple overlapping complements or fragments of the molecule 160 are created, e.g., fragments 130-1 and 130-2. As such, FIG. 4C illustrates obtaining a plurality of sequence reads, where each respective sequence read 128 in the plurality of sequence reads comprises a first portion 130 that corresponds to a subset of the molecule 160 and a common second portion 132 that forms a barcode that is independent of the sequence of the molecule 160 and that identifies a partition 404, in a plurality of partitions, in which the respective sequence read was formed (e.g., barcode sequence 132).

Although including sequence portions that are complementary to portions of the test nucleic acid 302, these constructs are generally referred to herein as comprising fragments of the sample test nucleic acid 302, having the attached barcode sequences. As will be appreciated, the replicated portions of the template sequences as described above are often referred to herein as "fragments" or molecules 160 of that template sequence. Notwithstanding the foregoing, however, the term "fragment" and the interchangeable term "molecule 160" encompasses any representation of a portion of the originating test nucleic acid sequence, e.g., a template or sample nucleic acid, including those created by other mechanisms of providing portions of the template sequence, such as actual fragmentation of a given molecule of sequence, e.g., through enzymatic, chemical or mechanical fragmentation. In preferred aspects, however, fragments (molecules 160) of a test nucleic acid sequence will denote replicated portions of the underlying sequence or complements thereof.

Figure 4D:
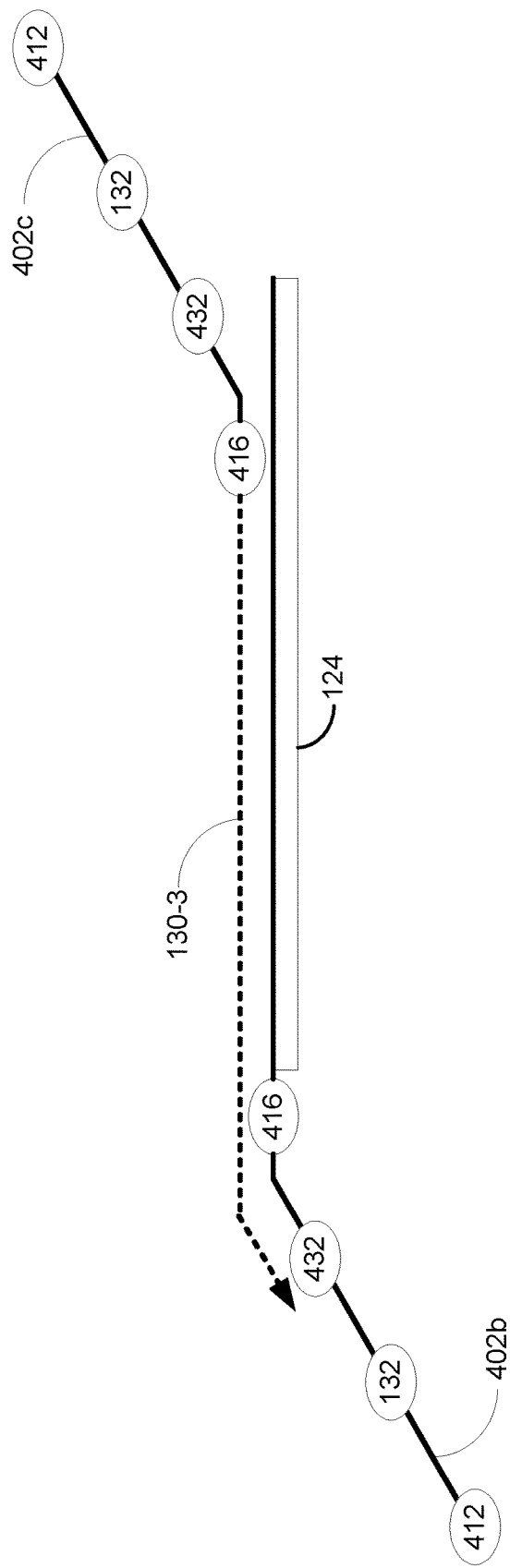
Figure 4E:
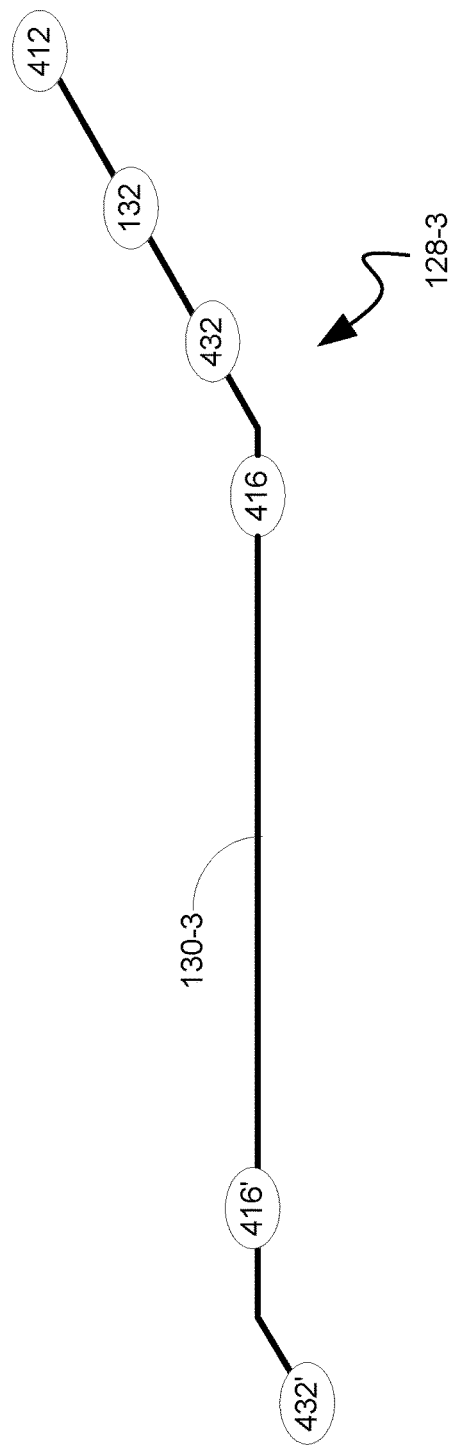

The barcoded nucleic acid molecules 160 of FIG. 4B may then be subjected to characterization, e.g., through sequence analysis, or they may be further amplified in the process, as shown in FIG. 4D. For example, additional oligonucleotides, e.g., oligonucleotide 402c, also released from bead 408, may prime the fragment 402b. In particular, again, based upon the presence of the random N-mer primer 416 in oligonucleotide 402c (which in many cases will be different from other random N-mers in a given partition) the oligonucleotide anneals with the fragment 402b, and is extended to create a complement 130-3 to at least a portion of fragment 402b which comprises a duplicate of a portion of the test nucleic acid sequence. Extension of the oligonucleotide 402b continues until it has replicated through the oligonucleotide portion 130 of fragment 402b. As noted elsewhere herein, and as illustrated in FIG. 4D, the oligonucleotides may be configured to promptly stop in the replication by the polymerase at a desired point, e.g., after replicating through sequences 416 and 412 of oligonucleotide 402b that is included within fragment. As described herein, this may be accomplished by different methods, including, for example, the incorporation of different nucleotides and/or nucleotide analogues that are not capable of being processed by the polymerase enzyme used. For example, this may include the inclusion of uracil containing nucleotides within the sequence region to prevent a non-uracil tolerant polymerase to cease replication of that region. As a result, referring to FIG. 4E, a sequence read 128-3 is created that includes the full-length oligonucleotide 402b at one end, including the barcode sequence 132, the attachment sequence 412, the R1 primer region 432, and the random N-mer sequence 416. At the other end of the sequence is included the complement 416' to the random N-mer of the first oligonucleotide 402, as well as a complement to all or a portion of the R1 sequence, shown as sequence 432'. The R1 sequence and its complement are then able to hybridize together to form a partial hairpin structure. As will be appreciated, because the random N-mers differ among different oligonucleotides, these sequences and their complements would not be expected to participate in hairpin formation, e.g., sequence 416', which is the complement to random N-mer 416, would not be expected to be complementary to random N-mer sequence 416b. This would not be the case for other applications, e.g., targeted primers, where the N-mers would be common among oligonucleotides within a given partition.

By forming these partial hairpin structures, it allows for the removal of first level duplicates of the sample sequence from further replication, e.g., preventing iterative copying of copies. The partial hairpin structure also provides a useful structure for subsequent processing of the created fragments, e.g., fragment 130-3.

All of the sequence reads 128 from multiple different partitions may then be pooled for sequencing on high throughput sequencers as described herein. Because each sequence read 128 is coded as to its partition of origin, the sequence of that sequence read may be attributed back to its origin based upon the presence of the barcode 132. Such sequence reads, and analysis of such sequence reads, form the basis of the disclosed nucleic acid sequencing dataset 126.

Figure 5:
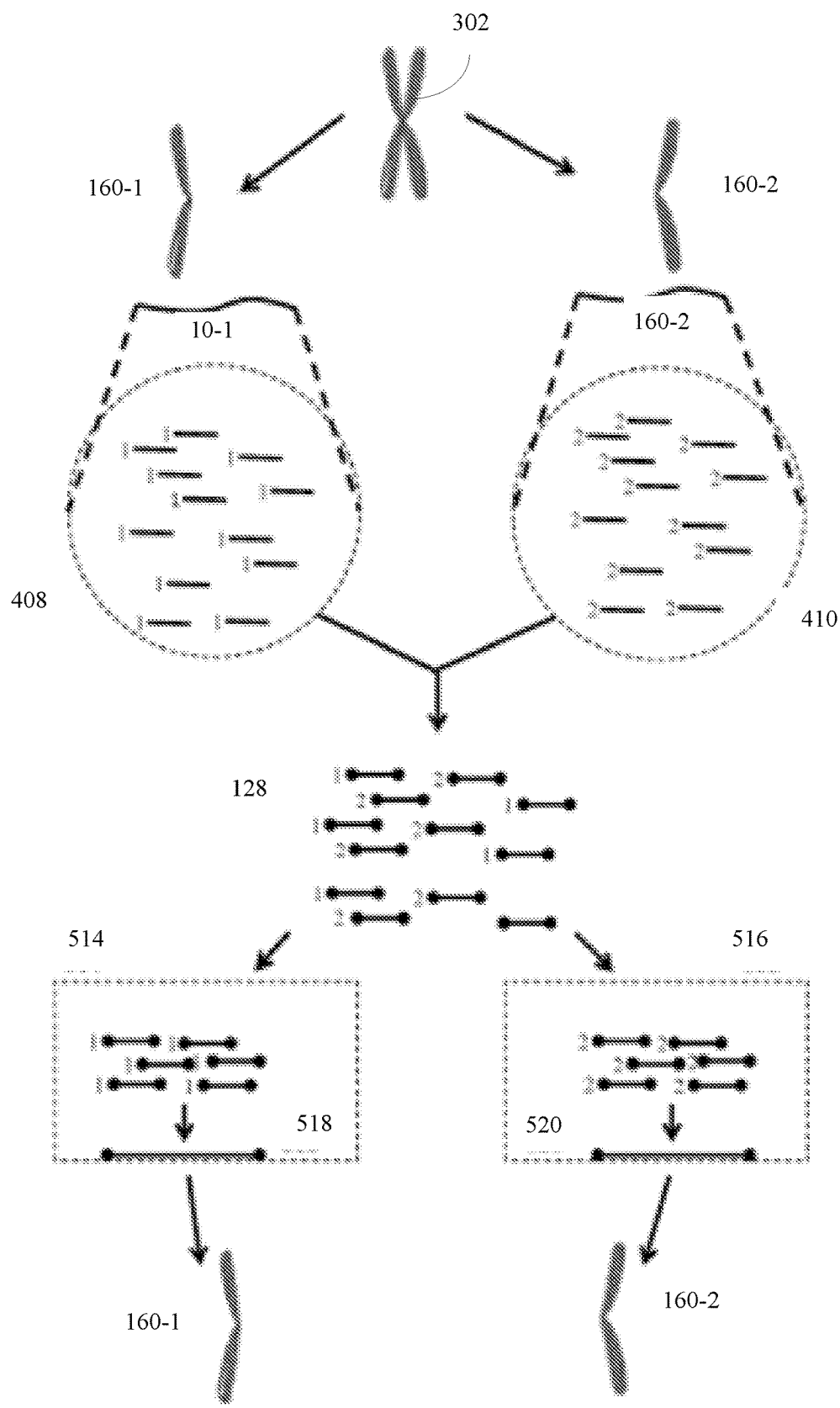
FIG. 5 illustrates a schematic for sequencing molecules that represent portions of a first string and/or second string in accordance with embodiments of the present disclosure.

This is schematically illustrated in FIG. 5. As shown in one example, a molecule 160-1 and a molecule 160-2 are each partitioned along with their own sets of barcode oligonucleotides 132 as described above. Within each partition, each molecule (160-1 and 160-2) is then processed to separately provide sequence reads 128 of the molecules 160-1 and 160-2 to form a respective set of sequence reads 514 and 516. This processing provides sequence reads 514 with a barcode sequence 132 that is the same for each of the sequence reads 514 derived from a particular first molecule 160-1. As shown, the set of sequence reads 514 is denoted by "1" while the set of sequence reads 516 is denoted by "2". A diverse library of barcodes may be used to differentially barcode large numbers of different sets of molecules 160. However, it is not necessary for every sequence read in a given partition to be barcoded with different barcode sequence. In fact, in many cases, multiple different molecules 160 may be processed concurrently to include the same barcode sequence. Diverse barcode libraries are described in detail elsewhere herein.

The sets of sequence reads may then be pooled for sequencing using, for example, sequence by synthesis technologies available from Illumina or Ion Torrent division of Thermo Fisher, Inc. Once sequenced, the sequence reads 128 can be attributed to their respective molecule set, e.g., as shown in aggregated reads, at least in part based upon the included barcodes, and optionally, and preferably, in part based upon the sequence of the fragment itself. The attributed sequence reads for each fragment set are then assembled to provide the assembled sequence for each sample molecule, e.g., sequences 518 and 520, which in turn, may be further attributed back to their respective original molecules (160-1 and 160-2). Methods and systems for assembling genomic sequences are described in, for example, U.S. Provisional Patent Application No. 62/017,589, filed Jun. 26, 2014, the full disclosure of which is hereby incorporated by reference in its entirety. In some embodiments, the sequence reads do not provide the entire sequence of the corresponding molecule 160. For instance, referring to FIG. 5, in some embodiments the set of sequencing reads 514 only provide sequencing information for 50 percent or less of the corresponding molecule 160, 40 percent or less of the corresponding molecule 160, 30 percent or less of the corresponding molecule 160 or 25 percent or less of the corresponding molecule 160.

In some embodiments, the biological sample is from a multi-chromosomal species and the test nucleic acid 302 comprises a plurality of nucleic acids collectively representing a plurality of chromosomes from the multi-chromosomal species. In some embodiments, the barcode 132 of each respective sequence read in the plurality of sequence reads encodes a unique predetermined value selected from the set $\{1, \ldots, 1024\}$, $\{1, \ldots 4096\}$, $\{1, \ldots, 16384\}$, $\{1, \ldots, 65536\}$, $\{1, \ldots, 262144\}$, $\{1, \ldots, 1048576\}$, $\{1, \ldots 4194304\}$, $\{1, \ldots, 16777216\}$, $\{1, \ldots, 67108864\}$, or $\{1, \ldots, 1 \times 10^{12}\}$ (210). For instance, consider the case in which the barcode sequence 132 is represented by a set of five nucleotide positions. In this instance, each nucleotide position contributes four possibilities (A, T, C or G), giving rise, when all five positions are considered, to $4 \times 4 \times 4 \times 4 = 1024$ possibilities. As such, the five nucleotide positions form the basis of the set $\{1, \ldots, 1024\}$. In other words, when the barcode sequence 132 is a 5-mer, the second portion 132 of each sequence read 128 encodes a unique predetermined value selected from the set $\{1, \ldots, 1024\}$. Likewise, when the barcode sequence 132 is represented by a set of six nucleotide positions, the six nucleotide positions collectively contribute $4 \times 4 \times 4 \times 4 \times 4 \times 4 = 4096$ possibilities. As such, the six nucleotide positions form the basis of the set $\{1, \ldots, 4096\}$. In other words, when the barcode sequence 132 is a 6-mer, the second portion 132 of each sequence read 128 encodes a unique predetermined value selected from the set $\{1, \ldots, 4096\}$.

In some embodiments, the barcode 132 of a sequence read in the plurality of sequence reads is localized to a contiguous set of oligonucleotides within the sequence read. In one such exemplary embodiment, the contiguous set of oligonucleotides is an N-mer, where N is an integer selected from the set $\{4, \ldots, 20\}$ (214). In other words, in some embodiments, the barcode 132 in, for instance FIG. 4B, panel B, is a contiguous set of nucleotide positions (e.g., 4 contiguous nucleotide positions, 5 contiguous nucleotide positions, 6 contiguous nucleotide positions, 7 contiguous nucleotide positions, 8 contiguous nucleotide positions, 9 contiguous nucleotide positions, 10 contiguous nucleotide positions, 11 contiguous nucleotide positions, 12 contiguous nucleotide positions, 13 contiguous nucleotide positions, 14 contiguous nucleotide positions, 15 contiguous nucleotide positions, 16 contiguous nucleotide positions, 17 contiguous nucleotide positions, 18 contiguous nucleotide positions, 19 contiguous nucleotide positions, or 20 contiguous nucleotide positions) within oligonucleotide tag 302 which ultimately becomes second portion 132 upon transcription of the test nucleic acid.

By contrast, in some embodiments, the barcode of a sequence read in the plurality of sequence reads is localized to a noncontiguous set of oligonucleotides within the sequence read. In one such exemplary embodiment, the predetermined noncontiguous set of nucleotides collectively consists of N nucleotides, where N is an integer in the set $\{4, \ldots, 20\}$. As an example, in some embodiments, referring to FIG. 4A, panel B, barcode sequence 132 comprises a first set of contiguous nucleotide positions at a first position in oligonucleotide tag 402 and a second set of contiguous nucleotide positions at a second position in oligonucleotide tag 402, that is displaced from the first set of contiguous nucleotide positions by a spacer. In one specific example, the barcode sequence 132 comprises $(X1)_n Y_z (X2)_m$, where X1 is n contiguous nucleotide positions, Y is a constant predetermined set of z contiguous nucleotide positions, and X2 is m contiguous nucleotide positions. In this example, the barcode in the second portion of the sequence read 128 produced by a schema invoking this exemplary barcode is localized to a noncontiguous set of oligonucleotides, namely $(X1)_n$ and $(X2)_m$. This is just one of many examples of noncontiguous formats for barcode sequence 132.

In some embodiments, the first sequence read in the plurality of sequence reads corresponds to a subset of the test nucleic acid that is 2×36 bp, 2×50 bp, 2×76 bp, 2×100 bp, 2×150 bp or 2×250 bp, where the terminology 2×N bp means that the sequence read has two reads of length N base pairs from a single piece of nucleic acid (e.g., from a text nucleic acid obtained from a biological sample) that are separated by an unspecified length. In some embodiments this unspecified length is between 200 to 1200 base pairs. In some embodiments, a first sequence read in the plurality of sequence reads represents at least 25 bp, at least 30 bp, at least 50 bp, at least 100 bp, at least 200 bp, at least 250 bp, at least 500 bp, less than 500 bp, less than 400 bp, or less than 300 bp of a single piece of nucleic acid (e.g., from a text nucleic acid obtained from a biological sample). (220).

As disclosed above barcodes 128 are used in a sequencing process to sequence and phase portions of a genome. In so doing, sequencing reads 128 of portions of the genome are obtained, where each such sequencing read 128 includes a bar code 132. Sequencing reads 128 that include overlapping portions of the genome are organized into larger molecules, with each such molecule 160 representing a portion of the genome. Moreover, single-nucleotide polymorphisms within the sequencing reads 128 are used to phase each such molecule into haplotypes. Once this is done, the systems and methods of the present disclosure are invoked in order to identify distal structural variants that are present in the genome of the subject whose genome is being sequenced and to properly haplotype these structural variants.

Figure 2A:
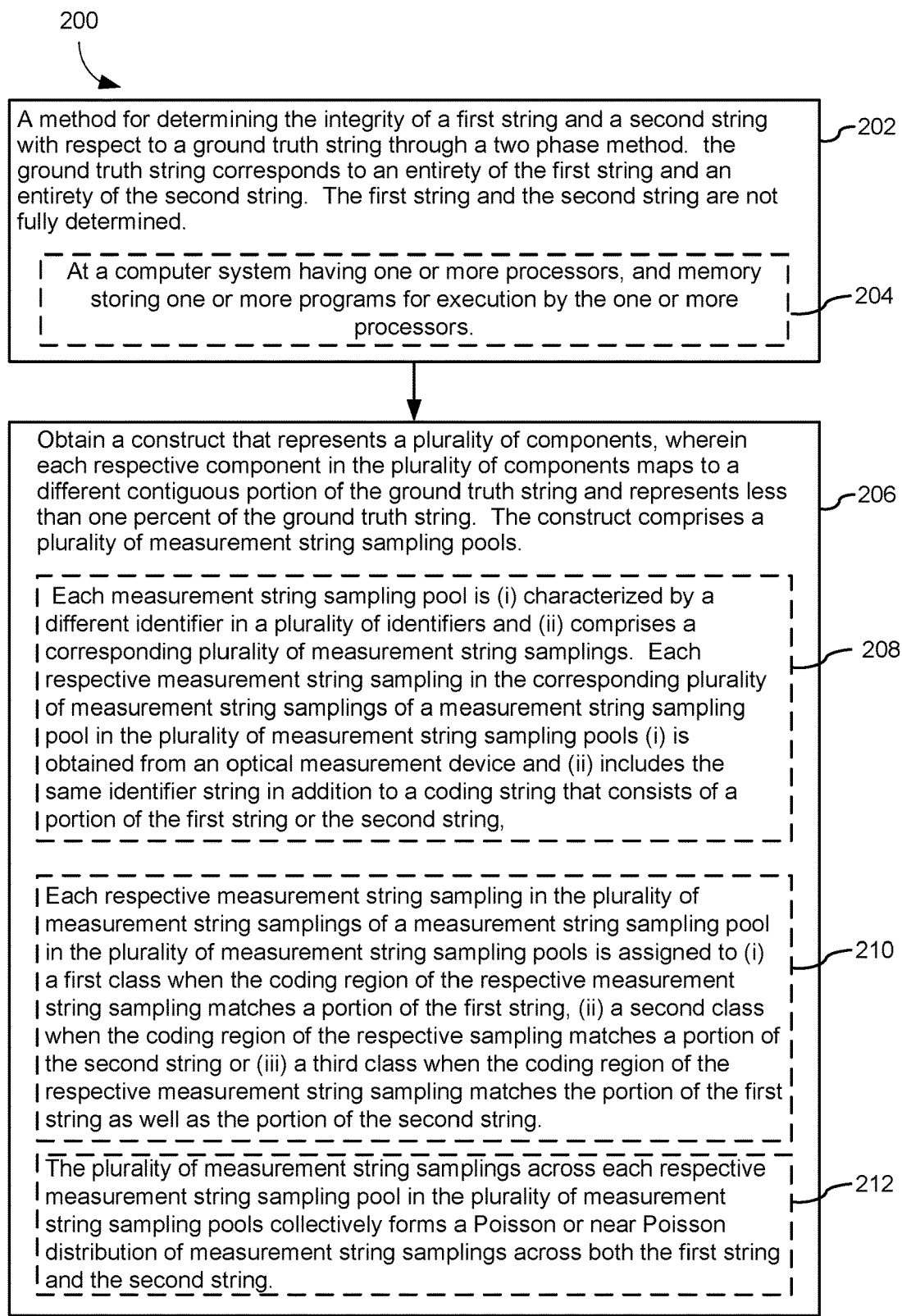
FIGS. 2A, 2B, and 2C illustrate a method of determining the integrity of a first string and a second string (e.g. elucidating a structural variation) with respect to a ground truth string through a two phase method in accordance with some implementations.

As discussed above, a construct (e.g., test nucleic acid sequencing data 126 is obtained that represents a plurality of components (e.g., molecules 160). Each respective component (e.g., molecule 160) in the plurality of components maps to a different contiguous portion of the ground truth string (e.g., human genome) and represents less than one percent of the ground truth string. The construct comprises a plurality of measurement string sampling pools (FIG. 2A; 206).

In some embodiments, the first string, the second string, the reference sequence, each component in the plurality of components, and each measurement string sampling in each plurality of measurement string samples is a base-four string. For example, in some such embodiments, each position in the first string, the second string, the reference sequence, each component in the plurality of components, and each measurement string sampling in each plurality of measurement string samples is one of adenosine "A", thymine "T," cytosine "C," and guanine "G."

In some embodiments, the ground truth string, the first string and the second string each include more than $3 \times 10^9$ positions. In other words, in some embodiments, the ground truth string, the first string and the second string each encode the human genome.

In some embodiments, each respective component (e.g., molecule 160) in the plurality of components comprises between 25,000 and 100,000 positions (e.g., 25,000 and 100,000 contiguous nucleotides).

In some embodiments, each respective component (e.g., molecule 160) in the plurality of components consists of between 25,000 and 100,000 positions (e.g., 25,000 and 100,000 contiguous nucleotides).

In some embodiments, the plurality of components (e.g., molecules 160) include components that map onto each position of the ground truth string. In other words, the plurality of components collectively provide full coverage for the ground truth string. Stated differently, in some embodiments the plurality of components collectively provide full coverage for the genome of the test sample. In some embodiments, this coverage is on average 2× or greater, meaning that, on average, each position in the ground truth string is encompassed by at least two different components in the plurality of components in the construct. In some embodiments, this coverage is on average 3 times or greater, 4 times or greater, 5 times or greater, or 10 times or greater meaning that, on average, each position in the ground truth string is encompassed by at least three different, four different, five different or ten different components in the plurality of components in the construct.

Referring to element 208 of FIG. 2A, in some embodiments, each measurement string sampling pool is (i) characterized by a different identifier (e.g., barcode 132) in a plurality of identifiers and (ii) comprises a corresponding plurality of measurement string samplings (e.g., sequence reads 128). Each respective measurement string sampling in the corresponding plurality of measurement string samplings of a measurement string sampling pool in the plurality of measurement string sampling pools (i) is obtained from an optical measurement device and (ii) includes the same identifier string in addition to a coding string that consists of a portion of the first string or the second string. For instance, the pool of sequence reads 514 of FIG. 5 constitute a measurement string sampling pool. They each have the same bar code 132.

In some embodiments, less than fifty percent of a component in the plurality of components is represented by measurement string samples in the plurality of measurement string sampling pools of the construct. In other words, in reference to FIG. 3, in some embodiments, the sequencing reads 128 that have the same barcode 132 only provide the sequence of a portion of a corresponding molecule 160. Thus, while in typical embodiments the molecules 160 provide full coverage of the test nucleic acid sequence 302 (e.g., first string and second string), the measurement string samples (sequence reads) that were generated from the molecules 160 do not provide full coverage of the molecules they were generated from. In some such embodiments, less than fifty percent of each component in the plurality of components of the construct (test nucleic acid sequencing data 126) is represented by measurement string samples in the plurality of measurement string sampling pools. In some embodiments, less than thirty percent of each component in the plurality of components of the construct (test nucleic acid sequencing data 126) is represented by measurement string samples (sequencing reads 128) in the plurality of measurement string sampling pools.

Referring to element 210 of FIG. 2A, in some embodiments, each respective measurement string sampling in the plurality of measurement string samplings of a measurement string sampling pool in the plurality of measurement string sampling pools is assigned to (i) a first class when the coding region of the respective measurement string sampling matches a portion of the first string, (ii) a second class when the coding region of the respective sampling matches a portion of the second string or (iii) a third class when the coding region of the respective measurement string sampling matches the portion of the first string as well as the portion of the second string. In some embodiments, the first class and the second class each indicate that the coding region encompasses a portion of the genome of the test subject that is heterozygous meaning that there are differences between the first string and the second string in the region encompassed by the measurement string sampling. As such, a given measurement string is assigned class 1 if it matches the first string in this region and is assigned class 2 if it matches the second string in this region. In some embodiments, the third class indicates that the coding region encompasses a portion of the genome of the test subject that is homozygous meaning that there are no differences between the first string and the second string in the region encompassed by the measurement string sampling. As such, a given measurement string is assigned class 3 if it matches both the first string and the second string in this region.

Referring to element 212, in some embodiments, the plurality of measurement string samplings across each respective measurement string sampling pool in the plurality of measurement string sampling pools collectively forms a Poisson or near Poisson distribution of measurement string samplings across both the first string and the second string. For instance, as illustrated in FIG. 3, the sequence reads 128 collectively form a Poisson or near Poisson distribution over the test nucleic acid 302 which represents the first string and the second string. It will be appreciated that, in fact the test nucleic acid is from a diploid subject and thus there are two copies the genome, the first copy being the first sting and the second copy being the second string.

Figure 2B:
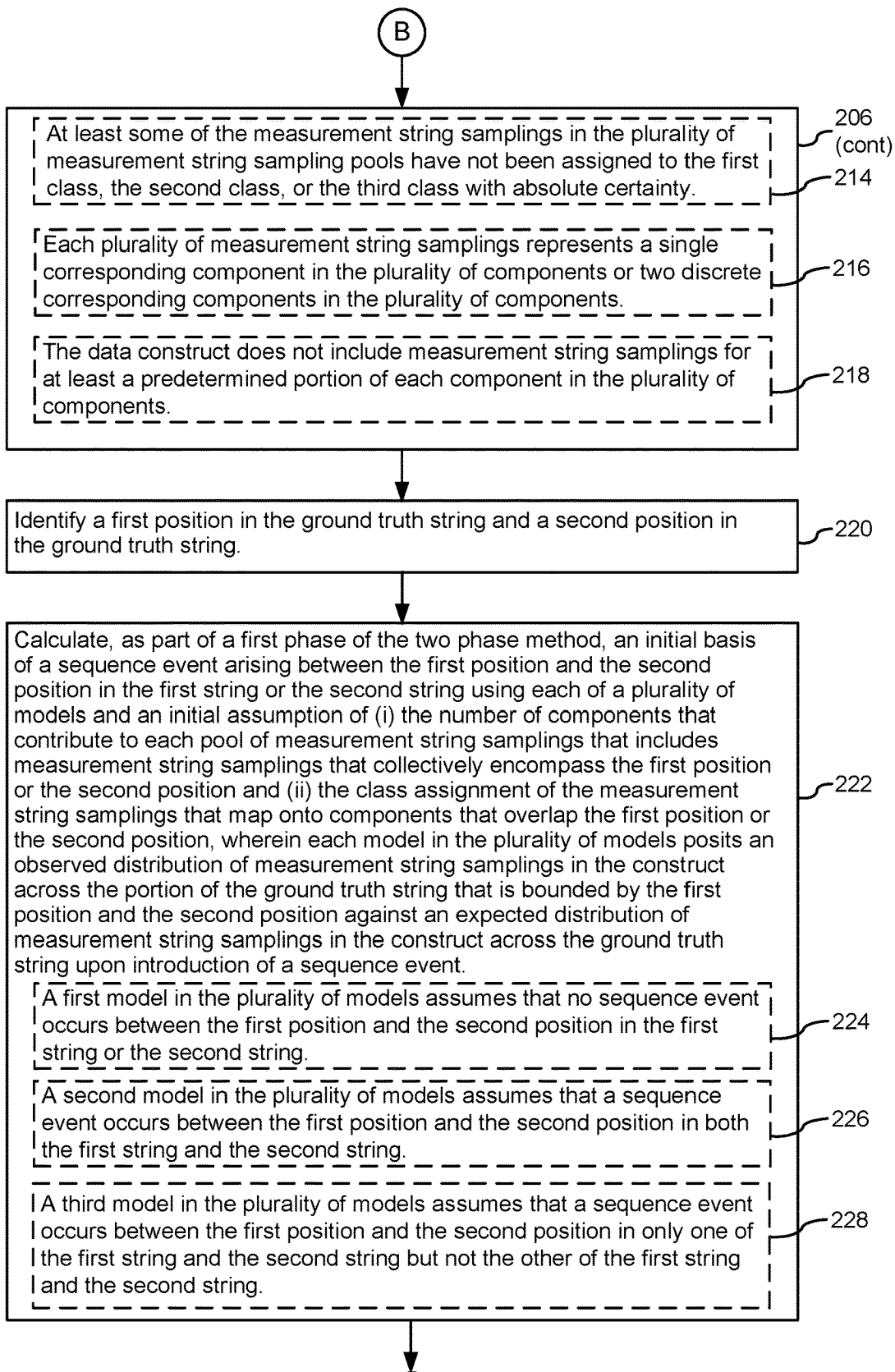
Figure 2C:
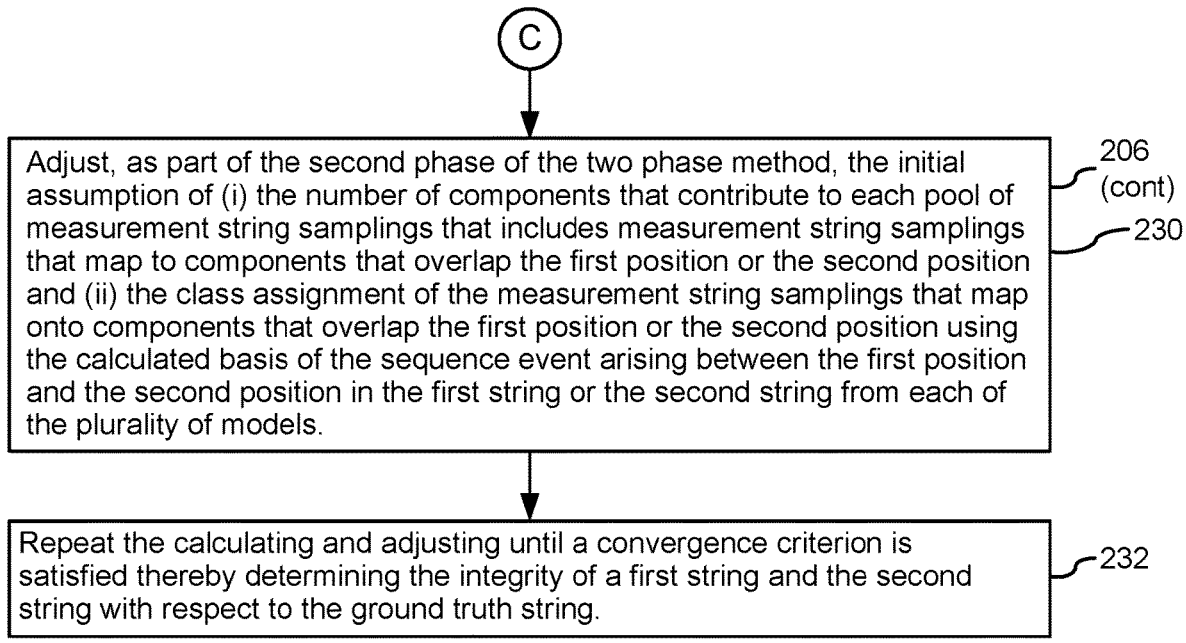

Referring to element 214 o FIG. 2B, in some embodiments, at least some of the measurement string samplings in the plurality of measurement string sampling pools have not been assigned to the first class, the second class, or the third class with absolute certainty. This is because, as highlighted in element 218 of FIG. 2B, the data construct (test nucleic acid sequencing data 126) does not include measurement string samplings (sequence reads 128) for at least a predetermined portion of each component (molecule 160) in the plurality of components of the construct. In fact, in some embodiments, less than 25 percent of the sequence of each molecule is represented by sequence reads in the dataset (construct). Moreover, because of this, the construct contains a latent variable, which is the number of molecules each measurement string sampling pool in fact represents. It is most likely the case that each measurement string sampling pool represents a single molecule 160 (component) due to the dilution parameters used to construct each partition, as described above. However, it is possible that two molecules 160 that are near each other in the ground truth string (genome) made their way into the same partition. It is even possible that three molecules 160 that are near each other in the ground truth string (genome) made their way into the same partition. However, such a possibility, and the possibility of even greater numbers of molecules 160 that are near each other in the genome are in the same partition are not considered in some embodiments. In some embodiments, each plurality of measurement string samplings is considered to either represent a single corresponding component (molecule 160) in the plurality of components or two discrete corresponding components (two molecules 160) in the plurality of components, with the latter possibility being more unlikely than the former possibility.

With the dataset (construct) in hand, with reference to element 220 of FIG. 2B, a search for first and second positions in the genome of the test subject that may signify a structural event (e.g., deletion, inversion, etc.) are identified. In other words, candidate regions with sufficient barcode overlap are identified. The goal of this process is to obtain a high-sensitivity/low-specificity list of potential structural candidates. With reference to FIG. 1, given two loci 166 in the genome, what is desired is a quick way to decide whether they share a significant number of common barcodes 128. In some embodiments, the list of these loci is provided to the next step of the algorithm, which uses a probabilistic calculation to make a more accurate prediction as to whether the observed barcode overlap is consistent with the presence of a structural variant.

Expected barcode overlap between distant loci. In some embodiments, the identification of a first position in the ground truth string and the second position in the ground truth string (first and second positions in the genome of the test subject) is performed on the basis that there is at least a threshold probability that a sequence event occurs in the first string or the second string between the first position and the second position, where the threshold probability is determined based upon an extent of overlap between measurement string samplings with common identifiers that map to the first position and the second position in the construct. For instance, if the two loci 166 are on different chromosomes or the distance between them is much larger than the average molecule length 160, then a binomial test can be used to determine if the observed barcode overlap between the loci is larger than expected by chance. Let $N_1$, $N_2$, and N be the observed number of barcodes at the first locus, the observed number of barcodes at the second locus, and the barcode diversity respectively. Then, the probability of observing n common barcodes between the two loci is governed by the binomial distribution:

$$\text{Binom}(n; N_1, N_2/N)$$

In some embodiments, a p-value cutoff is used to select all pairs of loci 164 for which the above probability is less than the cutoff. These loci pairs 164 serve as candidates for distal SVs. In some embodiments, the p-value cutoff is 0.1 or less, 0.05 or less, 0.01 or less, or 0.001 or less. In some embodiments, loci pairs 164 are identified using other statistical tests, such as those disclosed in Agresti, 1996, *An Introduction to Categorical Data Analysis*, John Wiley & Sons, Inc., New York, which is hereby incorporated by reference. In some embodiments, the p value valuation is used to pick the candidate loci pairs that have a decent chance of ultimately ending up in one of categories of structural variants that are being sought.

Expected barcode overlap between not so distant loci. The binomial test above assumes that the two loci 166 under consideration are independent in that no molecule 160 can span both loci. This assumption clearly does not hold when the distance d between two loci is in the order of the molecule length.

Given the count of barcodes on each of the loci and the distance between them, the expected number of common barcodes between the two loci is computed. In some embodiments, the probability that a molecule with barcode b present at locus X will reach locus X+d is computed as:

$$f_b(d) = P(b \text{ present at } X+d | b \text{ present at } X) = \text{sum}_{m:L(m)>d}(P(\text{molecule at } X \text{ is } m)P(m \text{ present at } X+d | m \text{ present at } X))$$

Here the sum is over molecules m 160 having barcode b (e.g., molecules 160 which include a sequencing read 128 having a barcode 132 b) with a length of molecule 160 $L(m) > d$. The first probability above, P(molecule at X is m), is $L(m)/\text{sum}_m L(m')$, where the summation is across all molecules 160 (components) having barcode b. The second is $(L(m)-d)/L(m)$. Simplifying provides $\text{sum}_{m:L(m)>d}(L(m)-d))/\text{sum}_{m'}(L(m'))$. In practice, good results are obtained by simplifying further to $\text{sum}_{m:L(m)>d}L(m)/\text{sum}_{m'}L(m')$.

Given two loci 166 at distance d apart from each other in the genome with $N_1$ and $N_2$ barcodes (respective barcode support lists 168) respectively, the expected barcode overlap between them is estimated as $$\min(N_1, N_2) \times f(d)$$

where $f(d) = \text{avg}_b f_b(d)$, in some embodiments. In some embodiments, $f(d)$ is precomputed for a range of values of d. In some embodiments, the time required to compute $f(d)$ is reduced by sampling a large number of barcodes instead of using all of them to compute the above average. In some embodiments, if the actual barcode overlap between the two loci exceeds the expected barcode overlap by a threshold amount, then the two loci are chosen for further analysis. In some embodiments, if the actual barcode overlap between the two loci is less than the expected barcode overlap by a threshold amount, then the two loci are chosen for further analysis.

In some embodiments, each respective locus position 166 has been phased and there is a set of barcodes at the respective locus that have been assigned to haplotype 1 (172) and barcodes that have been assigned to haplotype 2 (174). As such, each locus has been haplotyped. For instance, the barcodes of sequence reads across locus x (first position of ground truth string) have each been assigned to haplotype 1 or 2. Separately, the barcodes of sequence reads across locus y (second position of ground truth string) have each been assigned to haplotype 1 or 2. However, the barcodes of sequence reads across locus y are in a totally different region of the genome than the barcodes of sequence reads across locus x and it is uncertain how they match up. It is not the case that the assigned haplotype 1 of locus x is the assigned haplotype 1 of locus y. The haplotype assignment at locus x and y is independent of each other.

In some embodiments sequence reads 128 with the same barcode 132 overlap each other thereby forming molecules 160. Because of the overlap in sequence reads having the same barcode 132, it is possible to phase each molecule using the phase of the overlapping sequence reads. As such, each molecule is associated with a number of overlapping sequence reads having the same barcode and a haplotype 129. If the molecule represents a portion of the genome that is homozygous for all structural nucleotide polymorphisms in the represented portion of the genome, all the sequence reads for the molecule should be the same. If the molecule represents a portion of the genome that is heterozygous for all structural nucleotide polymorphisms in the represented portion of the genome, some of the sequence reads for the molecule will indicate a haplotype of 1 and other sequence reads for the molecule will indicate a haplotype of 2.

In some embodiments, the sequencing data 126 is acquired through a process in which genomic DNA is broken up into molecules 160, as described above with reference to FIGS. 3 and 4, and a limited number of such molecules is encapsulated in a sequencing partition. All sequence reads from this sequence partition have the same characteristic barcode 132 which serves to uniquely identify the partition from which the sequence reads were obtained and thus the molecules from the genome that were sequenced by the partition. In practice, hundreds, thousands, or millions of such partitions are formed, each containing a limited subset of molecules of the genome and each producing sequence reads with a unique barcode 132. In some embodiments, each such molecule 160 (component) represents between 25 kilobases and 100 kilobases of genomic DNA (ground truth string), between 40 kilobases and 80 kilobases of genomic DNA, or between 15 kilobases and 100 kilobases of genomic DNA. In some embodiments, each partition includes less than 20 such molecules, less than 15 such molecules or less than 10 such molecules where each such molecule is from a different portion of the genome. As a case in point, in a typical scale, there are 10 unique molecules in a partition, each encodes 50 kilobases of genomic DNA drawn from random locations of the genome and the total genomic DNA encodes $3.2 \times 10^9$ bases. This ensures that the probability that any two molecules 160 in the same partition (and thus having the same barcode 132) is very low. Because of this, it is possible to take all sequence reads (measurement string sampling) that have the same barcode 132, and overlap them with respect to a reference genome in order to identify the nucleic acid sequence of molecules 160. In some embodiments, the sequence reads 128 do not cover the entire molecule 160. In fact, in some embodiments, the sequence reads 128 only cover between 5 percent and 80 percent of a given molecule 160. In some embodiments, the sequence reads 128 only cover between 10 percent and 40 percent of a given molecule 160. In one specific embodiment, the sequence reads 128 cover about 20 percent of the sequence of a molecule 160. In typical embodiments where the sequence reads 128 for a given molecule 160 do not encompass the entire sequence of the molecule, the sequence reads 128 are each in random positions throughout the molecule 160. In typical embodiments, once the sequence reads 128 of a molecule 160 are identified through the barcodes 132, the sequence data 126 is interrogated for single nucleotide polymorphisms (SNPs) using conventional SNP calling algorithms.

Thus, through this sequencing process a number of molecules 160 are called. In some embodiments, for any given position in the genome, there are 10 or more molecules 160 (components), 20 or more molecules 160, 30 or more molecules 160, 50 or more molecules 160, 100 or more molecules 160, 150 or more molecules 160 or 200 or more molecules 160 called (e.g., that span the given position in the genome). Moreover, on average, the sequence reads 128 (measurement string samplings) for each of these molecules span at least 10 percent, at least 15 percent or at least 20 percent of each of the molecules 160. Thus, in a typical embodiment, for a given place in the genome on average there are 150 molecules 160 (represented by 150 different bar codes 132) that span the given place in the genome and for which there is sequence read 128 data for about 20% of the length of each of those molecules, giving rise to a read coverage of 150 times 20%, or 30×. From the relationships of SNPs observed in the vicinity of the given place in the genome, it is possible to start genotyping the given place in the genome into one or two haplotypes to explain the data. In other words, the sequence reads 128 of any given molecule 160 indicate a particular haplotype, and collectively, the genotype of each of the molecules 160 that span a given position in the genome are used to call the given position in the genome (e.g., as homozygous for haplotype 1, homozygous for haplotype 2, or heterozygous for haplotypes 1 and 2). In the case where the position is heterozygous, some of the molecules 160 spanning (and their corresponding barcodes) the given position in the genome will be for haplotype 1 and some of the molecules 160 spanning (and their corresponding barcodes) the given position in the genome will be for haplotype 2.

Figure 6:
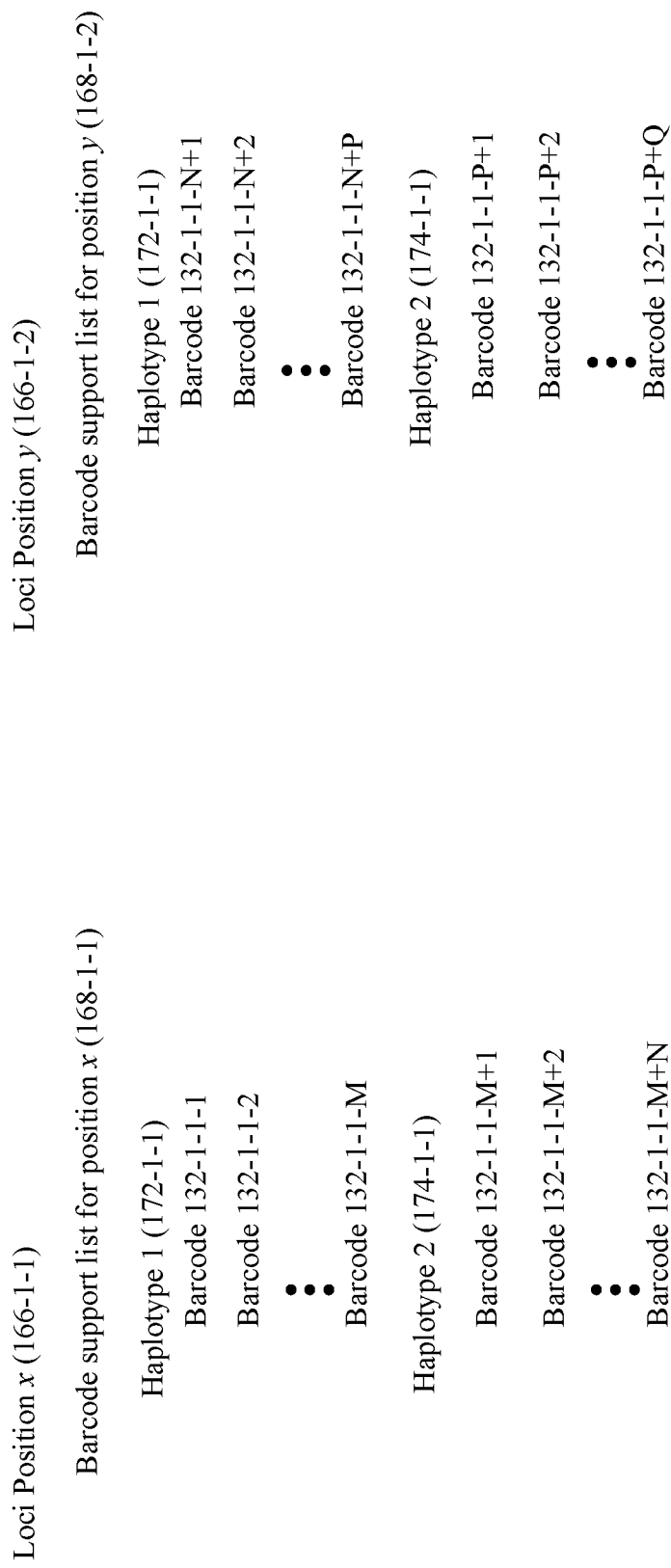
FIG. 6 illustrates the barcode support information for calling the haplotype of locus x and the haplotype of locus y that is collected in accordance with some embodiments of the present disclosure.

What is identified at this stage of the present disclosure are pairs of loci that have an unusual degree of overlap in common barcodes 132. In other words, referring to FIG. 6, test nucleic acid sequencing data 126 affords, for each locus pair x, y, a barcode support list 168-1-1 for position x and a barcode support list 1681-2 for position y. Each position x and y may be homozygous for one haplotype (haplotype "1" or "2") or heterozygous for two haplotypes (haplotype "1" and "2"). Each position x and y has a barcode support list 168 that provides the support for each of these haplotypes. Thus, at position x, there is a first list 172 of barcodes 132 that support haplotype 1 and a second list 174 of barcodes that support haplotype 2. Further, at position y, there is a third list 172 of barcodes 132 that support haplotype 1 and a fourth list 174 of barcodes that support haplotype 2. In some instances, any of the first, second, third, or fourth lists is null or empty. In some instances, each of the first, second, third, or fourth lists comprises several barcodes 132. In some embodiments, there is on the order of 150 different barcodes for position x and 150 different barcodes for position y, and there may or may not have some overlap between each list. Each barcode that spans positions x and y has a haplotype at position x and a haplotype at position y that may be the same or different.

As disclosed below, in some embodiments, a probabilistic model is used to determine whether the common barcodes between the lists at positions x and y arise due to a structural variation (e.g., a deletion, inversion, etc.) between the two loci in relation to a reference genome. It is further used to determine which haplotype at position x and position y the structural variation is between. For instance, consider the case where a structural variation is suspected between positions x and y and that each barcode 132 that is shared between positions x and y are on the same haplotype (e.g., haplotype 1) but none of the barcodes that are shared between positions x and y are on haplotype 2. This suggests that the structural variation arising between positions x and y is between haplotype 1 at position x and haplotype 1 at position y.

Probabilistic Model.

Setting Up a Maximum-Likelihood Problem.

Given two candidate loci for structural variation (e.g., a loci pair 164), a determination is made as to whether the observed sequencing reads 128 in the two loci are more consistent with the presence or the absence of a structural variation. Thus, with reference to element 222 of FIG. 2B, there is calculated, as part of a first phase of two phase method, an initial basis of a sequence event arising between the first position and the second position (e.g., a loci pair 164) in the first string or the second string using each of a plurality of models and an initial assumption of (i) the number of components (molecules 160) that contribute to each pool of measurement string samplings that includes measurement string samplings (sequence readings) that collectively encompass the first position (x of the loci pair) or the second position (y of the loci pair) and (ii) the class assignment of the measurement string samplings that map onto components that overlap the first position or the second position, where each model in the plurality of models posits an observed distribution of measurement string samplings (sequence readings) in the construct (dataset 126) across the portion of the ground truth string (genome) that is bounded by the first position and the second position against an expected distribution of measurement string samplings in the construct across the ground truth string upon introduction of a sequence event.

In particular, a model that maximizes the data (log-) likelihood is sought:

$$\log P(D; m) = \Sigma_b \log P(D_b; m)$$

Here, $D_b$ is the observed data from barcode b (at the loci of interest—the presence of the barcode at very distant loci is considered irrelevant). In other words, $D_b$ is a set of sequence reads 128 that each have the same barcode 132. Data from different barcodes are independent (conditioning on the model). Further, m is the model and comes from the discrete set of models comprising: (1) no structural variation (no structural variation or reference model), (2) homozygous structural variation at loci x and y, and (3) structural variation at loci x and y on haplotypes i and j respectively.

In the present disclosure, the nomenclature P(D; m) means, generally, the probability of observing data D, given the condition m. This model embodies the likelihood of observing some pattern of sequence reads in the genome for each given barcode.

The expression $\log P(D; m) = \Sigma_b \log P(D_b; m)$ therefore means that the probability that the test nucleic acid sequencing data 126 (construct) is explained by a given model is equivalent to the summation of the individual probabilities of the sequence reads 128 (measurement string samplings) for each respective barcode, over all respective barcodes 132, given the model.

Here, x and y is any loci pair 164 of the genome. However, as discussed above, in preferred embodiments, only a relatively small list of loci pairs 164 are considered based, for example, on barcode overlaps or read-pair support. The values i and j are in {0, 1} and denote the haplotype assignment of the breakpoints (loci) x and y. In some embodiments, it is further assumed that if x and y are on the same phase block, then i and j must be equal (e.g., the structural variant-calling cannot redefine phase blocks). In some embodiments, this set of structural variant models is further refined based on the type of the structural variant, as described in more detail below.

There are two sets of latent variables within the test nucleic acid sequencing data 126 (construct): $H_b^{x,y}$ the haplotype assignment of barcode b at loci x and y, and $M_b$, the number of molecules 160 from which the sequencing reads 128 with barcode 132 b were generated. For simplicity, in some embodiments, it is assumed that $M_b$ can be at most two, since it is extremely unlikely that there are more than two molecules 160 from the same locus in the same partition (or that we had multiple partitions with the same barcode).

The following provides a non-limiting summary of notation in accordance with some embodiments:

D is the observed data (positions of sequencing reads 128, their barcodes 132, and their assigned haplotype 129) in the loci under consideration;

$D_b$ is the data (e.g. read positions) from barcode b;

$D_{b_1 \ldots k}$ is a subset of $D_b$ comprising the first k sequence reads from barcode b;

$R_b$ is the event that there is no structural variant on barcode b (or that b was generated from the reference);

$SV_b^{x,y}$ is the event that there is a structural variant between positions x and y on the haplotype that generated barcode b (i.e., the haplotype that barcode b has been assigned, with sequence reads for bar code b spanning positions x and y);

$SV_{ij}^{x,y}$ is the event that there is a structural variant at positions x, y on haplotypes i and j respectively, where i, j∈{0, 1}, in other words, the structural variation arises between haplotype i at position x and at haplotype j at position y;

α is the expected number of sequence reads 128 per base pair in the genome, based on the assumption that that sequence reads 128 are generated from a Poisson distribution with rate α (uniform across the genome, uniform across the ground truth string, etc.);

$P_L(l)$ is the probability of having a molecule 160 of length l (in some embodiments an empirical molecule length distribution is used); and $L_{max}$ is the maximum possible length of an input molecule 160.

As noted above, $R_b$ means that there is no structural variant on barcode b (or that b was generated from the reference). In other words, $R_b$ means that there is no structural variant on the haplotype of barcode B. Thus, either there is no structural event at the locus encompassed by barcode B or, if there is a structural event at the locus encompassed by barcode B, the structural event occurred on the other haplotype at locus encompassed by barcode B.

Referring to elements 224 through 228 of FIG. 2B, in some embodiments, a first model in the plurality of models assumes that no sequence event occurs between the first position and the second position in the first string or the second string. In some embodiments, a second model in the plurality of models assumes that a sequence event occurs between the first position and the second position in both the first string and the second string. In some embodiments, a third model in the plurality of models assumes that a sequence event occurs between the first position and the second position in both the first string and the second string. For computation of three models considered by the present disclosure (1) no structural variation (no structural variant or reference model), (2) homozygous structural variation at loci x and y, or (3) structural variation at loci x and y on haplotypes i and j respectively, some useful probabilities are introduced. Pursuant to the relationship $$\log P(D;m) = \Sigma_b \log P(D_b;m)$$

each of these models is individually evaluated against the test nucleic sequence data for the sequence reads 128 of each barcode 132. In other words, the probabilities for the observed distribution of the sequence reads 128 for each barcode 132 with sequence reads that span loci x and y given the models set forth below is summed for each model to give an overall probability of each of the possible models given the sequence read data.

Probability of a molecule. Let $x_{b_1} \leq x_{b_2} \leq \ldots \leq x_{b_n}$ be the positions of the sequence reads 128 from a single molecule 160 with barcode 132 b. In some embodiments, it is assumed that the sequence reads 128 are generated from a single molecule 160 with hidden length l. The distances $x_{b_{i+1}} - x_{b_i}$ can be considered the waiting times between events of a Poisson process. As such, the log-probability of observing the molecule 160 $P_m(n, d)$ is:

$$\log P_m(x_{b_1}, x_{b_2}, \ldots, x_{b_n}) =$$

$$\log\left[\sum_{\ell \geq x_{b_n} - x_{b_1}} P_L(\ell) \alpha e^{-\alpha(\ell - (x_{b_n} - x_{b_1}))} \prod_{i=1}^{n-1} \alpha e^{-\alpha(x_{b_{i+1}} - x_{b_i})}\right] =$$

$$\log\left[\alpha^n \prod_{i=1}^{n-1} e^{-\alpha(x_{b_{i+1}} - x_{b_i})} \sum_{\ell \geq x_{b_n} - x_{b_1}} P_L(\ell) e^{-\alpha(\ell - (x_{b_n} - x_{b_1}))}\right] =$$

$$\log\left[\alpha^n e^{-\alpha(x_{b_n} - x_{b_1})} \sum_{\ell \geq x_{b_n} - x_{b_1}} P_L(\ell) e^{-\alpha(\ell - (x_{b_n} - x_{b_1}))}\right] =$$

$$\log\left[\alpha^n \sum_{\ell \geq x_{b_n} - x_{b_1}} P_L(\ell) e^{-\alpha \ell}\right] =$$

$$n\log\alpha + \log addexp_{\ell \geq x_{b_n} - x_{b_1}} [\log P_L(\ell) - \alpha\ell]$$

where log addexp is the log of the sum of the exponentials of the arguments. Intuitively, the probability of observing the molecule 160 is the product of the following probabilities: (i) the probability of getting a molecule 160 of length e given that the molecule length was greater than $x_{b_n} - x_{b_1}$, (ii) the probability of observing waiting times $x_{b_{i+1}} - x_{b_i}$, and (iii) the probability of observing no sequence reads 128 in a length $l - (x_{b_n} - x_{b_1})$. These probabilities are then summed over all possible lengths $l \geq x_{b_n} - x_{b_1}$ in some embodiments. Since $P_m$ only depends on the observed length $d = x_{b_n} - x_{b_1}$ and the number of sequence reads n from a single molecule 160 with barcode 132 b, below the (overloaded) notation $P_m(n, d)$ is used.

Thus, referring to FIG. 7A, given a molecule 160, a plurality of sequence reads 128 would arise from the molecule 160. The above models capture what these sequence reads 128 would look like, in other words, their positions in the genome (e.g. their distribution, where they would show up). As part of this, the length of the molecule 160 is estimated from the observed test nucleic acid sequencing data 126. Thus, given length e, sequence reads inside that interval can be generated. If the molecule 160 is long, one is not expected to only observe sequence reads 128 on only one half of the molecule. Rather, what is expected is that there should be a uniform distribution of sequence reads 128 across the extent of the molecule 160. Now, consider the case where FIG. 7A is the reference or native state of the genome of the test subject and referring to FIG. 7B a structural event, relative to FIG. 7A in the form of a deletion, between positions x and y that are spanned by the molecule 160 has occurred such that region 3202 is missing from molecule 160. In such instances, a model that supports absence of sequence reads in the region of 702 will exhibit a higher probability of supporting the test nucleic acid sequencing data 126 observed from the sequencing the molecule 160 of FIG. 7B. As FIG. 7 illustrates, different types of structural variants will give rise to different predicted patterns of sequence reads. For instance, as discussed above, the coverage of sequence reads 128 to a given molecule 160 is a predetermined known quantity, such as twenty percent. This gives rise to an expected average distance between sequence reads 128 within a molecule 160. In other words, this gives rise to an expected average distance between sequence reads 128 that have the same barcode 132. Structural variations disrupt this pattern of sequence read spacing 128. The models below predict the different patterns of sequence reads across molecules 160 given different structural variations. Because there are several different types of structural variants, several different models are evaluated as discussed below. For instance, an inversion between x and y may have the effect of bringing the two positions closer together. A model that predicts such an inversion would then better explain the actual measured sequence read data, namely the pattern of sequence reads 128 across positions x and y for each molecule 160 that spans these two positions then a model that does not have such an inversion.

Barcode likelihood assuming no structural variant (model type 1). The likelihood of the data from barcode b assuming that all of the data from barcode b were generated from a single molecule 160 from the reference is:

$$P(D_b|M_b=1;R_b) = P_m(n,d)$$

if $x_{b_1}, \ldots, x_{b_n}$ are all on the same chromosome and $x_{b_n} - x_{b_1} < L_{max}$, where $L_{max}$ is the maximum possible length of an input molecule 160. In other words, the probability is a function of the number of sequence reads n having barcode "b" observed and the observed length d of the molecule 160, where observed length d is the total distance separating the first and last observed sequence read having barcode b within the genome. Otherwise $P(D_b|M_b=1; R_b)=\varepsilon$, where $\varepsilon$ is a disfavored penalty value for the model.

Similarly, for the case where the sequence reads for barcode b were generated from two different molecules, the model is given as:

$$P(D_b|M_b=2;R_b)=\Sigma_{k=2}^{n-1} P(D_{b_1\ldots k}|M_{b_1\ldots k}=1; R_{b_1\ldots k})P(D_{b_{k+1}\ldots n}|M_{b_{k+1}\ldots n}=1;R_{b_{k+1}\ldots n})$$

More accurately, summation over all possible splits into two disjoint subsets is performed in some embodiments. However, in some embodiments, this adds too much complexity (especially given how unlikely barcode collisions are and how few molecules 160 are typically within a partition), so in preferred embodiments the assumption is made that molecules 160 cannot overlap but can "touch."

In the above equations, $M_b=1$ assumes that all sequence reads with the barcode "b" arose from a single molecule 160. Further, $M_b=2$ assumes that the sequence reads with the barcode "b" arose from either a first molecule 160 or a second molecule 160 that are proximate to each other in the reference genome (ground truth string). That is, they are near each other or are overlapping each other and were sequenced in the same partition and thus all sequence reads from the two molecules have the same barcode b.

As noted above, in some embodiments, each partition typically includes 5 or more molecules 160. However, in typical instances, these molecules are very far apart in the genome. In cases where two of the molecules 160 either overlap or are close to each other (e.g., in the vicinity of considered loci positions x and y), it is necessary to model this using the above equation where $M_b=2$. In other words, because there is always the possibility that that the distribution of sequence reads having barcode b is explained by a single molecule 160 or two proximate molecules 160, the case of no structural variation is modeled using both equations ($M_b=1$ and $M_b=2$) set forth above.

In some embodiments, the model for likelihood assuming no structural variant (model type 1), is a weighted average of:

$$P(D_b|M_b=1;R_b)=P_m(n,d)$$

and $$P(D_b|M_b=2;R_b)=\Sigma_{k=2}^{n-1} P(D_{b_1\ldots k}|M_{b_1\ldots k}=1; R_{b_1\ldots k})P(D_{b_{k+1}\ldots n}|M_{b_{k+1}\ldots n}=1;R_{b_{k+1}\ldots n})$$

where the $M_b=2$ probability contributes less weight to the weighted averages because it requires the less likely assumption that two molecules contributed to the observed pattern of sequence reads for a given barcode b. Here the measurement string samplings $b_{1\ldots k}$ (sequence reads $b_{1\ldots k}$) are deemed to map onto a first component (molecule 160) and the measurement string samplings $b_{k+1\ldots n}$ (sequence reads $b_{k+1\ldots n}$) are deemed to map onto a second component.

Barcode likelihood assuming a homozygous structural variant (model type 2). Model type 2 seeks to address the situation in which there is a homozygous structural variant. In other words, model type 2 provides the probability of the observed data for barcode b where the sequence data came from a single molecule 160 and b equals one and there is a structural variation between positions x and y on the haplotypes that barcode b is assigned to at both positions x and y, as illustrated in FIG. 7B. The likelihood assuming that the data from barcode b were generated from a structural variant haplotype $P(D_b|M_b=1; SV_b^{x,y})$ depends on the type of the structural variant (e.g., deletion as illustrated in FIG. 7B, inversion as illustrated in FIG. 7C, duplication, large-scale translocation, etc). FIG. 7B illustrates the case where the structural variant is a deletion. Each of these structural variant types are considered in turn below.

Deletions. Assume that the structural variant is a deletion between x and y (x<y) and that $x_{b_i}<x\leq x_{b_{i+1}}$ and $x_{b_j}<y\leq x_{b_{j+1}}$.

If $x>x_{b_n}$ or $y<x_{b_1}$, meaning that x is after the position of the last observed sequence read having barcode b (and so therefore y is as well) or that y is before the position of the first sequence read (and so therefore x is as well), then $P(D_b|M_b=1; SV_b^{x,y})=P(D_b|M_b=1; R_b)$ meaning that barcode b does not support a structural variant between x and y. In some embodiments, it is assumed that the structural variants are independent from each other on the basis that at most there is one structural variant within the length of a molecule 160. If $i\neq j$, this means that the molecule 160 has sequence reads 128 inside the deletion, so $P(D_b|M_b=1, SV_b^{x,y})$ is set to penalty $\varepsilon$ meaning that $P(D_b|M_b=1, SV_b^{x,y})$ is unlikely and disfavored.

If none of the above holds, we have $x_{b_1}\leq x_{b_2}\leq \ldots \leq x_{b_i}<x<y\leq x_{b_{i+1}}\leq \ldots \leq x_{b_n}$. In other words, there are observed sequences reads to the left of x and to the right of y and what is now tested is the presence of a deletion between x and y. Let d=y-x be the length of the deleted sequence. Then $P(D_b|M_b=1; SV_b^{x,y})=P_m(x_{b_1}, x_{b_2}, \ldots, x_{b_i}, x_{b_{i+1}}-d, \ldots, x_{b_n}-d)=P_m(n, x_{b_n}-x_{b_1}-d)$. In other words, the model tests how likely is the sequence read data (the observed positions of the sequence reads 128 having the given barcode b) under the idea that there is a deletion between genomic positions x and y of length d.

The above three scenarios assume that the data $D_b$ is explained by a single molecule 160. If, on the other hand there are two molecules 160, $P(D_b|M_b=2; SV_b^{x,y})$ would better explain the data. To compute $P(D_b|M_b=2; SV_b^{x,y})$, all splits of the sequence reads 128 from barcode b into two chunks are considered. Like before, in some embodiments, this is simplified by only considering non-overlapping chunks:

$$P(D_b|M_b=2;SV_b^{x,y})=\Sigma_{k=2}^{n-1} P(D_{b_1\ldots k}|M_{b_1\ldots k}=1;SV_b^{x,y})P(D_{b_{k+1}}|M_{b_{k+1}}=1;SV_b^{x,y}).$$

Depending on where $x_k$ is with respect to x and y each of the probabilities above is equal to the probability under either the reference or the structural variant model.

Inversions. An inversion is illustrated in FIG. 7C where it is seen that region 704b is inverted relative to 704a the reference genome. As can be seen, this causes an observable redistribution of the positions of the sequence reads. Notably sequence read 128-3 is now closer to sequence read 128-4. In FIG. 7, it is assumed that each sequence read illustrated is for the same bar code b. To compute model 2 in which the structural variant arises from an inversion, in some embodiments, the assumption is made that the structural variant is an inversion between x and y (x<y) and that $x_{b_i}<x\leq x_{b_{i+1}}$ and $x_{b_j}<y\leq x_{b_{j+1}}$. In such instances, there are two cases: $x_{b_1}\leq x_{b_2}\leq \ldots \leq x_{b_i}<x<x_{b_{i+1}}\leq \ldots \leq x_{b_n}<y$ (reads span x but end before y) or $x\leq x_{b_1}\leq \ldots \leq x_{b_j}<y\leq \ldots \leq x_{b_n}$ (reads start after x and span y). In the first case, $P(D_b|M_b=1; SV_b^{x,y})=P_m(x_{b_1}, x_{b_2}, \ldots, x_{b_i}, d-x_{b_n}, d-x_{b_{n-1}}, \ldots, d-x_{b_{i+1}})=P_m(n,x-x_{b_1}+y-x_{b_{i+1}})=P_m(n,d-x_{b_1}-x_{b_{i+1}})$, where d=x+y. The second case is similar.

Alternatively, the observed sequence reads 128 are entirely before x, entirely after y, entirely between x and y, or the sequence reads span across x and y. In such instances, $P(D_b|M_b=1; SV_b^{x,y})=P(D_b|M_b=1; R_b)$ meaning that the sequence reads for barcode b do not support the proposition of an inversion between x and y.

Duplications. In considering the application of model 2 where the structural variant is a duplication, in some embodiments, the assumption is made that the structural variation is a duplication between x and y (x<y) and that $x_{b_i} \leq x < x_{b_{i+1}}$ and $x_{b_j} \leq x < x_{b_{j+1}}$. If $x < x_{b_i}$ and $y > x_{b_j}$, then the sequence reads 128 span the duplication and $P((D_b|M_b)=1, SV_b^{x,y})=P_m(n,d+y-x)$. If $x < x_{b_i}$ and $y > x_{b_n}$ (sequence reads 128 entirely within the duplication), then $P((D_b|M_b)=1, SV_b^{x,y})=\max(P_m(n, x_{b_n}-x_{b_1}),\max_j P_m n, y-x-x_{b_{j+1}}+x_{b_j}))$. Otherwise, $P((D_b|M_b)=1, SV_b^{x,y})=((D_b|M_b)=1, R_b)$.

Large-scale translocations. In considering the application of model 2 where the structural variant is a large-scale translocation, in some embodiments, only the case where $x_{b_1}, \ldots x_{b_n}$ are generated from two different chromosomes or $x_{b_n}-x_{b_1}>L_{max}$ is considered. In such instances, the sequence reads 128 are split into two groups $x'_{b_1}, \ldots, x'_{b_{n'}}$, $x''_{b_1}, \ldots, x''_{b_{n''}}$ such that n'+n"=n. Each group contains the subset of sequence reads closer to x and y respectively.

If any of the two sets of sequence reads 128 above are empty then $P((D_b|M_b)=1, SV_b^{x,y})=P((D_b|M_b)=1, R_b)$ If $x'_{b_1} < x$ and $x''_{b_{n''}} > y$ then $P((D_b|M_b)=1, SV_b^{x,y})=P_m(n, x-x'_{b_1}+x''_{b_{n''}}-y)$.

All cases where all sequence reads from the first set are on the same side of x and all reads from the second set are on the same side of y are similar. Otherwise, $P((D_b|M_b)=1, SV_b^{x,y})=\varepsilon$, where $\varepsilon$ is a penalty value that discourages this model under these conditions.

EM. In some embodiments, an EM approach, or other two phased method, is used to maximize the likelihood of the models described herein. In some embodiments, this involves repeatedly conditioning on the latent variables to compute the maximum likelihood model and then getting a posterior estimate of the latent variables.

M-Step: Likelihood Conditioning on the Latent Variables (Element 222 of FIG. 2B).

Homozygous reference. With reference to element 224 of FIG. 2B and as further explained above, in some embodiments, the likelihood of the data under the homozygous reference model (model 1) is:

$$\prod_b \sum_{c=1}^{2} P(D_b | M_b = c, R_b) P(M_b = c)$$

In particular, in some such embodiments, the first model comprises computing:

$$\prod_b \sum_{c=1}^{2} P(D_b | M_b = c, R_b) P(M_b = c)$$

where, each b is a different identifier for a measurement string sampling pool that comprises measurement string samplings that encompass the first position and the second position, $P(M_b=1)$ is the probability that the measurement string sampling pool that comprises measurement string samplings for identifier b arises from a single component, $P(M_b=2)$ is the probability that the measurement string sampling pool that comprises measurement string samplings for identifier b arises from two different components, $P(D_b|M_b=1; R_b)=P_m(n, d)$ for a respective measurement string sampling pool having the common identifier b where n is the number of measurement string samplings in the measurement string sampling pool for identifier b, $M_b=1$ indicates that the measurement string sampling pool for identifier b is deemed to map to a single component in the plurality of component, d is a length of the component, and $$P(D_b | M_b = 2; R_b) = \sum_{k=2}^{n-1} P(D_{b_1 \ldots k} | M_{b_1 \ldots k} = 1; R_{b_1 \ldots k})$$

$$P(D_{b_{k+1} \ldots n} | M_{b_{k+1} \ldots n} = 1; R_{b_{k+1} \ldots n})$$

Where the measurement string samplings $b_{1 \ldots k}$ are deemed to map onto a first component and the measurement string samplings $b_{k+1 \ldots n}$ are deemed to map onto a second component.

Homozygous SV. With reference to element 226 of FIG. 2B and as further explained above, in some embodiments, the likelihood of the data under the homozygous SV model (model 2) is:

$$\prod_b \sum_{c=1}^{2} P(D_b | M_b = c, SV_b^{x,y}) P(M_b = c)$$

In particular, in some embodiments, the second model comprises computing.

$$\prod_b \sum_{c=1}^{2} P(D_b | M_b = c, SV_b^{x,y}) P(M_b = c)$$

where each b is a different identifier for a measurement string sampling pool that comprises measurement string samplings that encompass the first position and the second position, $P(D_b|M_b=1; SV_b^{x,y})$ is the probability that a sequence event occurs between the first position and the second position in both the first string and the second string assuming that the measurement string sampling pool that comprises measurement string samplings for identifier b arises from a single component, $P(M_b=1)$ is the probability that the measurement string sampling pool that comprises measurement string samplings for identifier b arises from a single component, and $P(M_b=2)$ is the probability that the measurement string sampling pool that comprises measurement string samplings for identifier b arises from two different components.

In some embodiments, this is computed for deletions, inversions, duplications, and large scale translocations. In some embodiments, the second model is computed separately for at least two different possible sequence events in the group consisting of a deletion between the first position (x) and second position (y), an inversion of a region between the first position (x) and second position (y), a duplication between the first and second position, and a translocation between the first and second region.

In some embodiments, the second model is computed separately for at least three different possible sequence events in the group consisting of a deletion between the first and second position, an inversion of a region between the first and second region, a duplication between the first and second position, and a translocation between the first and second region.

In some embodiments, the second model is computed separately for (i) a deletion between the first and second position, (ii) an inversion of a region between the first and second region, (iii) a duplication between the first and second position, and (iv) a translocation between the first and second region.

Heterozygous structural variant. Referring to element 228 of FIG. 2B, in some embodiments, a third model in the plurality of models assumes that a sequence event occurs between the first position and the second position in only one of the first string and the second string but not the other of the first string and the second string in the case of a heterozygous structural variant:

$$P(D_b; m) = \sum_{i,j \in [0,1]^2} \sum_{c=1}^{2} P(D_b \mid H_b^{x,y} = (i,j), M_b = c; m) P(H_b^{x,y} = (i,j), M_b = c; m)$$

where m is the model (reference or structural variant), $$P(D_b | H_b^{x,y}=(i,j), M_b=1; SV_{i,j}^{x,y}) = P(D_b | SV_b^{x,y}, M_b=1),$$
and
$$P(D_b | H_b^{x,y} \neq (i,j), M_b=1; SV_{i,j}^{x,y}) = P(D_b | R_b, M_b=1).$$

To compute $P(D_b | H_b^{x,y} = (i), M_b = 2; SV_{i,j}^{x,y})$, in some embodiments, computation is initiated with the case where x and y are on the same phase block, so i and j are equal:

$$P(D_b \mid H_b^{x,y} = (i,i), M_b = 2; SV_{i,i}^{x,y}) =$$
$$\sum_{k=2}^{n-1} P\left(D_{b_1 \ldots k} \mid H_{b_1 \ldots k}^{x,y} = (i,i), M_b = 1; SV_{i,i}^{x,y}\right)$$
$$P\left(D_{b_{k+1} \ldots n} \mid H_{b_1 \ldots k}^{x,y} = (i,i), M_b = 1; SV_{i,i}^{x,y}\right)$$

Here the sum is taken over all ways of splitting the reads from b, $x_1, x_2, \ldots, x_n$ into two (non-empty) sequences $x_1, \ldots, x_k$ and $x_{k+1}, \ldots, x_n$. $D_{b_1 \ldots k}$ and $D_{b_{k+1} \ldots n}$ are the sets of reads resulting from such a split. Depending where $x_k$ is with respect to x $$P(D_{b_1 \ldots k} | H_{b_1 \ldots k}^{x,y} = (i,i), M_b = 1; SV_b^{x,y})$$

is either $P(D_{b_1 \ldots k} | R_{b_1 \ldots k}, M_{b_1 \ldots k} = 1)$ or $P(D_{b_1 \ldots k} | SV_{b_1 \ldots k}^{x,y}, M_{b_1 \ldots k} = 1)$. The likelihood of the second chunk of data is similar.

If x and y are on different phase blocks, then i and j can be different. In some embodiments, the assumption is made that the only valid split is the one that assigns the points closer to x to haplotype i and the points closer toy to haplotype. The computation is then similar to the case above.

E-step: Posterior of the latent variables. Referring to element 230 of FIG. 2C, there is adjusted, as part of the second phase of the two phase method, the initial assumption of (i) the number of components that contribute to each pool of measurement string samplings that includes measurement string samplings that map to components that overlap the first position or the second position and (ii) the class assignment of the measurement string samplings that map onto components that overlap the first position or the second position using the calculated basis of the sequence event arising between the first position and the second position in the first string or the second string from each of the plurality of models. In some embodiments, this is embodiments this is performed as an E step of EM, where $$P(H_b^{x,y}=(i,j), M_b=c | D_b; m) \propto P(D_b | H_b^{x,y}=(i,j), M_b=c; m)$$
$$P(H_b^{x,y}(i,j), M_b=c).$$

Here, all that is needed is a prior on the latent variables. In some embodiments, the assumption is made that $$P(H_b^{x,y}=(i,j), M_b=c) = P(H_b^{x,y}=(i,j)) P(M_b=c)$$

The expectation-maximization algorithm generally, is described in Moon, 1996, "The expectation-maximization algorithm," IEEE Signal Processing Magazine 13(6), pp 47-60, which is hereby incorporated by reference. To compute $P(H_b^{x,y}=(i,j))$ $p_b^x(0)$, $p_b^x(1)$ is denoted the probability that barcode b at locus x is phased on haplotype 0 or 1 respectively in some embodiments. In some embodiments, the assumption is made that these probabilities are precomputed during SNP phasing of the data 126 prior to invoking expectation-maximization. If b is un-phased at x, then $p_b^x(0)$ is set to 0.5 or to the fraction of barcodes 132 that are phased to haplotype 0 at locus x. If x and y are in the same phase set, then $P(H_b^{x,y}=(i))=p_b^x(i)$ if i=j, and $P(H_b^{x,y}=(i,j))=0$ otherwise. If x and y are on different phase blocks then $P(H_b^{x,y}=(i,j))=p_b^x(i)p_b^y(j)$.

In some embodiments, to compute $P(M_b=c)$, where $p_{ov}$ is denoted the probability of having two overlapping molecules in the same partition, the probability that the sequence reads 128 with barcode b coming from a single molecule 160 is the product of the probability of generating a molecule greater than the observed length and the probability that there is no molecule overlap: $P(M_b=c)=\Sigma_{\ell \geq x_{b_n} - x_{b_1}} P_L(\ell)(1-p_{ov})$ and $P(M_b=2)=1-P(M_b=1)$.

As a result of the execution of the method illustrated in FIG. 2, one of the models will support one of possible scenarios (no structural variation event arising between x and y, a homogenous structural variation arising between x and y, or a heterozygous structural variation arising between x and y) better than the other models. In this way, the integrity of a first string and the second string with respect to the ground truth string is determined. In other words, in this way, a determination is made as to whether a structural variation arises between two points in the first string relative to the ground truth string as well as the same corresponding two points in the second string relative to the ground truth string. In some embodiments, the disclosed expectation maximization approach to maximizing the likelihood of each possible model, or some subset of each possible model, for structural variations that could arise between two loci position to thereby determine the integrity of a first string and the second string with respect to the ground truth string is computationally expensive. For example, in some embodiments, a computer having one or more processors each have a clock cycle of greater than one gigahertz takes more than two seconds, more than five seconds, more than one minute, or more than 10 minutes to execute the method illustrated in FIG. 2. In some embodiments, the convergence criterion is repetition of steps 222 and 230 a predetermined number of times, e.g., two times, three times, four times etc. In some embodiments, the convergence criterion is no update to the initial assumptions during the last instance of the steps 222 and 230.

Computing SV phasing scores. In some embodiments, a score is assigned to the haplotype assignment of the structural variant as:

$$\frac{P(D; SV_{i,j}^{x,y})}{\sum_{(i,j) \in [0,1]^2} P(D; SV_{i,j}^{x,y})}.$$

Conclusion

Plural instances may be provided for components, operations or structures described herein as a single instance. Finally, boundaries between various components, operations, and data stores are somewhat arbitrary, and particular operations are illustrated in the context of specific illustrative configurations. Other allocations of functionality are envisioned and may fall within the scope of the implementation(s). In general, structures and functionality presented as separate components in the example configurations may be implemented as a combined structure or component. Similarly, structures and functionality presented as a single component may be implemented as separate components. These and other variations, modifications, additions, and improvements fall within the scope of the implementation(s).

It will also be understood that, although the terms "first," "second," etc. may be used herein to describe various elements, these elements should not be limited by these terms. These terms are only used to distinguish one element from another. For example, a first object could be termed a second object, and, similarly, a second object could be termed a first object, without changing the meaning of the description, so long as all occurrences of the "first object" are renamed consistently and all occurrences of the "second object" are renamed consistently. The first object and the second object are both objects, but they are not the same object.

The terminology used herein is for the purpose of describing particular implementations only and is not intended to be limiting of the claims. As used in the description of the implementations and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined (that a stated condition precedent is true)" or "if (a stated condition precedent is true)" or "when (a stated condition precedent is true)" may be construed to mean "upon determining" or "in response to determining" or "in accordance with a determination" or "upon detecting" or "in response to detecting" that the stated condition precedent is true, depending on the context.

The foregoing description included example systems, methods, techniques, instruction sequences, and computing machine program products that embody illustrative implementations. For purposes of explanation, numerous specific details were set forth in order to provide an understanding of various implementations of the inventive subject matter. It will be evident, however, to those skilled in the art that implementations of the inventive subject matter may be practiced without these specific details. In general, well-known instruction instances, protocols, structures and techniques have not been shown in detail.

The foregoing description, for purpose of explanation, has been described with reference to specific implementations. However, the illustrative discussions above are not intended to be exhaustive or to limit the implementations to the precise forms disclosed. Many modifications and variations are possible in view of the above teachings. The implementations were chosen and described in order to best explain the principles and their practical applications, to thereby enable others skilled in the art to best utilize the implementations and various implementations with various modifications as are suited to the particular use contemplated.

What is claimed is:

1. A computing system, comprising:
   one or more processors; and
   memory, the memory storing one or more programs to be executed by the one or more processors, the one or more programs comprising instructions for determining whether a structural variation occurs at a first locus or a second locus in a plurality of loci, with respect to a reference genome, wherein
   the instructions comprise instructions for:
   (A) obtaining a data construct that represents a plurality of nucleic acid fragments, wherein
      each respective nucleic acid fragment in the plurality of nucleic acid fragments maps to a portion of the reference genome and represents less than one percent of the reference genome,
      the data construct comprises a plurality of sequence read pools,
      each sequence read pool is (i) characterized by a different identifier string in a plurality of identifier strings and (ii) comprises a corresponding plurality of sequence reads,
      each respective sequence read in the corresponding plurality of sequence reads of a sequence read pool in the plurality of sequence read pools (i) is obtained from an optical measurement device and (ii) includes the same identifier string in addition to a coding string that comprises a portion of the first or second locus,
      each respective sequence read in the plurality of sequence reads of a sequence read pool in the plurality of sequence read pools is assigned to (i) a first class when the coding region of the respective sequence read matches a portion of the first locus, (ii) a second class when the coding region of the respective sampling matches a portion of the second locus or (iii) a third class when the coding region of the respective sequence read matches the portion of the first locus as well as the portion of the second locus,
      the data construct does not include sequence reads for at least a predetermined portion of each nucleic acid fragment in the plurality of nucleic acid fragments;
   (B) calculating an initial basis of the structural variation at the first or second locus using each of a plurality of models and an initial assumption of (i) the number of nucleic acid fragments that contribute to each pool of sequence reads that includes sequence reads that collectively encompass the first or second locus and (ii) the class assignment of the sequence reads that map onto nucleic acid fragments that overlap the first or second locus;

(C) adjusting the initial assumption using the calculated basis of the structural variation occurring at the first or second locus from each of the plurality of models using an expectation- maximization algorithm; and (D) repeating the calculating (B) and adjusting (C) until a convergence criterion is satisfied thereby determining whether the structural variation occurs at the first or second locus.

2. The computing system of claim 1, wherein the instructions further comprise identifying the first locus and the second locus on the basis that there is at least a threshold probability that the structural variation occurs in the first locus or the second locus at wherein the threshold probability is determined based upon an extent of overlap between sequence reads with common identifiers that map to the first locus and the second locus in the data construct.

3. The computing system of claim 1, wherein the reference genome includes more than $3 \times 10^{9}$ nucleotides.

4. The computing system of claim 3, wherein each respective nucleic acid fragment in the plurality of nucleic acid fragments comprises between 25,000 and 100,000 nucleotides.

5. The computing system of claim 1 wherein more than twenty nucleic acid fragments in the plurality of nucleic acid fragments map onto each nucleotide position of the first locus and the second locus.

6. The computing system of claim 5, wherein less than fifty percent of a nucleic acid fragment in the plurality of nucleic acid fragments is represented by sequence reads in the plurality of sequence read pools.

7. The computing system of claim 5, wherein less than fifty percent of each nucleic acid fragment in the plurality of nucleic acid fragments is represented by sequence reads in the plurality of sequence read pools.

8. The computing system of claim 5, wherein less than thirty percent of each nucleic acid fragment in the plurality of nucleic acid fragments is represented by sequence reads in the plurality of sequence read pools.

9. The computing system of claim 1, wherein
each respective model m in the plurality of models is computed as $\Sigma_b \log P(D_b; m)$,
$\Sigma_b \log P(D_b; m)$ is a summation of a plurality of probabilities for a plurality of sequence read pools that span the first and second locus, each respective sequence read pool in the plurality of sequence read pools characterized by a different unique identifier b, and
each probability in the plurality of probabilities is the probability of the observed spacing of sequence reads in the sequence read pool having the common identifier b given model m.

10. The computing system of claim 1, wherein a model in the plurality of models comprises computing:

$$\prod_b \sum_{c=1}^{2} P(D_b \mid M_b = c, R_b) P(M_b = c)$$

wherein
each b is a different identifier for a sequence read pool that comprises sequence reads that encompass the first locus and the second locus,
$P(M_b=1)$ is the probability that the sequence read pool that comprises sequence_reads for identifier b arises from a single nucleic acid fragment,
$P(M_b=2)$ is the probability that the sequence read pool that comprises sequence reads for identifier b arises from two different nucleic acid fragments,
$P(D_b|M_b=1; R_b)=P_m(n, d)$ for a respective sequence read pool having the common identifier b wherein,
n is the number of sequence reads in the sequence read pool for identifier b,
$M_b=1$ indicates that the sequence read pool for identifier b is deemed to map to a single nucleic acid fragment in the plurality of nucleic acid fragments,
d is a length of the nucleic acid fragment, and $$P(D_b \mid M_b = 2; R_b) = \sum_{k=2}^{n-1} P(D_{b_1 \ldots k} \mid M_{b_1 \ldots k} = 1; R_{b_1 \ldots k})$$
$$P(D_{b_{k+1} \ldots n}} \mid M_{b_{k+1} \ldots n} = 1; R_{b_{k+1} \ldots n})$$

wherein the sequence reads $b_{1 \ldots k}$ are deemed to map onto a first nucleic acid fragment and the measurement string samplings $b_{k+1 \ldots n}$ are deemed to map onto a second nucleic acid fragment.

11. The computing system of claim 1, wherein a model in the plurality of models comprises computing:

$$\prod_b \sum_{c=1}^{2} P(D_b \mid M_b = c, SV_b^{x,y}) P(M_b = c)$$

wherein
each b is a different identifier for a sequence read pool that comprises sequence reads that encompass the first locus and the second locus,
$P(D_b|M_b=1; SV_b^{x,y})$ is the probability that the structural variation occurs in both the first locus and the second locus assuming that the sequence read pool that comprises sequence reads for identifier b arises from a single nucleic acid fragment,
$P(M_b=1)$ is the probability that the sequence read pool that comprises sequence reads for identifier b arises from a single nucleic acid fragment, and
$P(M_b=2)$ is the probability that the sequence read pool that comprises sequence reads for identifier b arises from two different nucleic acid fragments.

12. The computing system of claim 11, wherein the model is computed separately for at least two different possible types of the structural variation in the group consisting of a deletion occurring at one of the first locus and the second locus, an inversion occurring in one of the first locus and the second locus, a duplication occurring at one of the first locus and the second locus, and a translocation occurring between the first locus and second locus.

13. The computing system of claim 11, wherein the model is computed separately for (i) a deletion occurring at one of the first locus and the second locus, (ii) an inversion occurring in one of the first locus and the second locus, (iii) a duplication occurring at one of the first locus and the second locus, and (iv) a translocation occurring between the first locus and second locus.

14. The computing system of claim 1, wherein the identifier encodes a unique predetermined value selected from the set $\{1, \ldots, 1024\}$, selected from the set $\{1, \ldots, 4096\}$, selected from the set $\{1, \ldots, 16384\}$, selected from the set $\{1, \ldots, 65536\}$, selected from the set $\{1, \ldots, 262144\}$, selected from the set $\{1, \ldots, 1048576\}$, selected from the set {1, ..., 4194304}, selected from the set {1, ..., 16777216}, selected from the set {1, ..., 67108864}, or selected from the set {1, ..., 1×10$^{12}$}.

15. The computing system of claim 1, wherein the convergence criterion is that the adjusting fails to change the initial assumption using the calculated basis of the structural variation occurring in the first locus or the second locus from each of the plurality of models from a prior instance of the calculating (B).

16. The computing system of claim 1, wherein the plurality of nucleic acid fragments comprises ten thousand nucleic acid fragments.

17. The computing system of claim 1, the instructions further comprising:
   (E) repeating the calculating (B), adjusting (C), and repeating (D) for a different pair of first and second loci in the plurality of loci.

18. The computing system of claim 1, wherein,
   a first model in the plurality of models assumes that the structural variation does not occur at the first and the second locus,
   a second model in the plurality of models assumes that the structural variation occurs at both the first and the second locus, and
   a third model in the plurality of models assumes that the structural variation occurs at only one of the first and second locus but not the other of the first and second locus.

19. A non-transitory computer readable storage medium storing one or more programs configured for execution by a computer, the one or more programs comprising instructions for determining whether a structural variation occurs at a first locus or a second locus in a plurality of loci, with respect to a reference genome, and the instructions comprising instructions for:
   (A) obtaining a data construct that represents a plurality of nucleic acid fragments, wherein
      each respective nucleic acid fragment in the plurality of nucleic acid fragments maps to a portion of the reference genome and represents less than one percent of the reference genome,
      the data construct comprises a plurality of sequence read pools,
      each sequence read pool is (i) characterized by a different identifier string in a plurality of identifier strings and (ii) comprises a corresponding plurality of sequence reads,
      each respective sequence read in the corresponding plurality of sequence reads of a sequence read pool in the plurality of sequence read pools (i) is obtained from an optical measurement device and (ii) includes the same identifier string in addition to a coding string that consists of a portion of the first locus or the second locus,
      each respective sequence read in the plurality of sequence reads of a sequence read sampling pool in the plurality of sequence read pools is assigned to (i) a first class when the coding region of the respective sequence read matches a portion of the first locus, (ii) a second class when the coding region of the respective sequence read matches a portion of the second locus or (iii) a third class when the coding region of the respective sequence read matches the portion of the first locus as well as the portion of the second locus,
      the data construct does not include sequence reads for at least a predetermined portion of each nucleic acid fragment in the plurality of nucleic acid fragments;
   (B) calculating an initial basis of the structural variation at the first or second locus using each of a plurality of models and an initial assumption of (i) the number of nucleic acid fragments that contribute to each pool of sequence reads that includes sequence reads that collectively encompass the first or second locus and (ii) the class assignment of the sequence reads that map onto nucleic acid fragments that overlap the first or second locus;
   (C) adjusting the initial assumption the first or second locus from each of the plurality of models using an expectation-maximization algorithm; and
   (D) repeating the calculating (B) and adjusting (C) until a convergence criterion is satisfied thereby determining whether the structural variation occurs at the first or second locus.

20. The non-transitory computer readable storage medium of claim 19, wherein,
   a first model in the plurality of models assumes that the structural variation does not occur at the first and the second locus,
   a second model in the plurality of models assumes that the structural variation occurs at both the first and the second locus, and
   a third model in the plurality of models assumes that the structural variation occurs at only one of the first and second locus but not the other of the first and second locus.

21. A method of determining whether a structural variation occurs at a first locus or a second locus in a plurality of loci string with respect to a reference genome, the method comprising:
   (A) obtaining a data construct that represents a plurality of nucleic acid fragments, wherein
      each respective nucleic acid fragment in the plurality of nucleic acid fragments maps to a portion of the reference genome and represents less than one percent of the reference genome,
      the data construct comprises a plurality of sequence read pools,
      each sequence read pool is (i) characterized by a different identifier string in a plurality of identifier strings and (ii) comprises a corresponding plurality of sequence reads,
      each respective sequence read in the corresponding plurality of sequence reads of a sequence read pool in the plurality of sequence read pools (i) is obtained from an optical measurement device and (ii) includes the same identifier string in addition to a coding string that consists of a portion of the first locus or the second locus,
      each respective sequence read in the plurality of sequence reads of a sequence read pool in the plurality of sequence read pools is assigned to (i) a first class when the coding region of the respective sequence read matches a portion of the first locus, (ii) a second class when the coding region of the respective sampling matches a portion of the second locus or (iii) a third class when the coding region of the respective sequence read matches the portion of the first locus as well as the portion of the second locus,
      the data construct does not include sequence reads for at least a predetermined portion of each nucleic acid fragment in the plurality of nucleic acid fragments;

(B) calculating an initial basis of the structural variation at the first or second locus using each of a plurality of models and an initial assumption of (i) the number of nucleic acid fragments that contribute to each pool of sequence reads that includes sequence reads that collectively encompass the first or second locus and (ii) the class assignment of the sequence reads that map onto nucleic acid fragments that overlap the first or second locus, (C) adjusting the initial assumption using the calculated basis of the structural variation occurring at the first locus or the second locus from each of the plurality of models using an expectation-maximization algorithm; and (D) repeating the calculating (B) and adjusting (C) until a convergence criterion is satisfied thereby determining whether the structural variation occurs at the first or second locus.

22. The method of claim 21, wherein, a first model in the plurality of models assumes that the structural variation does not occur at the first and the second locus, a second model in the plurality of models assumes that the structural variation occurs at both the first and the second locus, and a third model in the plurality of models assumes that the structural variation occurs at only one of the first and second locus but not the other of the first and second locus.

* * * * *